(12) United States Patent
Tharaux et al.

(10) Patent No.: US 10,344,279 B2
(45) Date of Patent: *Jul. 9, 2019

(54) METHODS FOR THE PREVENTION AND THE TREATMENT OF EXTRACAPILLARY GLOMERULONEPHRITIS

(71) Applicants: INSERM (Institut National de la Sante et de la Recherche Medicale), Paris (FR); Universite Paris Descartes, Paris (FR)

(72) Inventors: Pierre-Louis Tharaux, Paris (FR); Carole Henique-Greciet, Paris (FR)

(73) Assignees: INSERM (INSTITUT NATIONAL DE LA SANTÉ ET DE LA RECHERCHE MÉDICALE), Paris (FR); UNIVERSITÉ PARIS DESCARTES, Paris (FR)

( * ) Notice: Subject to any disclaimer, the term of this patent is extended or adjusted under 35 U.S.C. 154(b) by 55 days.

This patent is subject to a terminal disclaimer.

(21) Appl. No.: 15/672,384

(22) Filed: Aug. 9, 2017

(65) Prior Publication Data

US 2017/0342415 A1 Nov. 30, 2017

Related U.S. Application Data

(62) Division of application No. 15/112,577, filed as application No. PCT/EP2015/051275 on Jan. 22, 2015, now Pat. No. 9,771,584.

(30) Foreign Application Priority Data

Jan. 23, 2014 (EP) ..................................... 14305094

(51) Int. Cl.
*A61K 48/00* (2006.01)
*C12N 15/11* (2006.01)
*C07H 21/02* (2006.01)
*C07H 21/04* (2006.01)
*C12N 15/113* (2010.01)
*A61K 31/713* (2006.01)
(Continued)

(52) U.S. Cl.
CPC ........ *C12N 15/113* (2013.01); *A61K 31/7088* (2013.01); *A61K 31/713* (2013.01); *C12Q 1/68* (2013.01); *C12Q 1/6883* (2013.01); *G01N 33/6893* (2013.01); *C12N 2310/113* (2013.01); *C12Q 2600/158* (2013.01); *C12Q 2600/178* (2013.01); *G01N 2800/347* (2013.01)

(58) Field of Classification Search
CPC .. C12Q 1/68; C12Q 1/6883; C12Q 2600/158; C12Q 2600/178; A61K 31/7088; A61K 31/713; C12N 15/11; C12N 15/113; C12N 2310/113; G01N 33/6893; G01N 2800/347
See application file for complete search history.

(56) References Cited

U.S. PATENT DOCUMENTS 9,771,584 B2 * 9/2017 Tharaux ............... C12Q 1/6883

OTHER PUBLICATIONS

H-Y Lin (Up-Regulation of MIR-92A by STAT3 Oncogene Promotes Invasiveness of Lung Cancer Cells, Master Thesis, Jun. 2012).*

(Continued)

*Primary Examiner* — Terra C Gibbs
(74) *Attorney, Agent, or Firm* — W&C IP

(57) ABSTRACT

The present invention relates to the prevention and the treatment of extracapillary glomerulonephritis such as rapidly progressive glomerulonephritis and collapsing glomerulonephritis.

Figure 1:
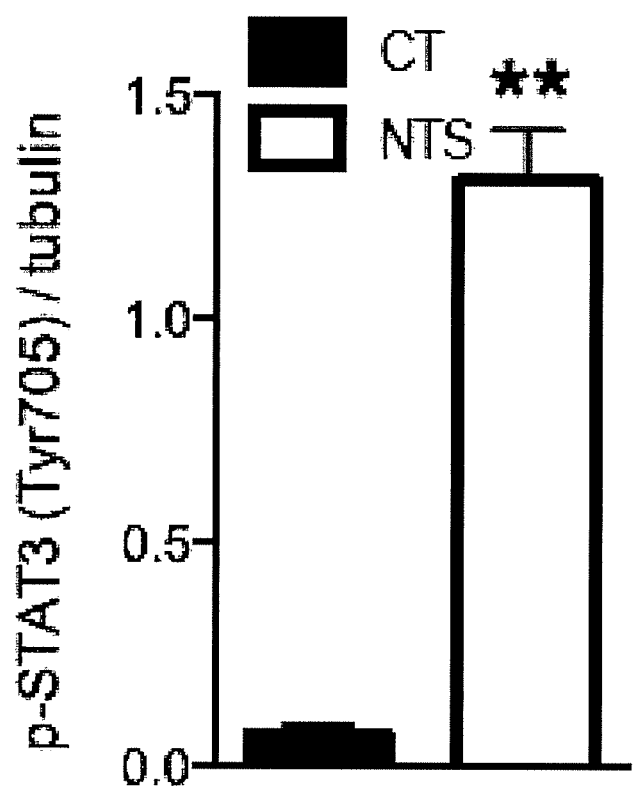

7 Claims, 16 Drawing Sheets
Specification includes a Sequence Listing.

(51) Int. Cl.
*A61K 31/7088* (2006.01)
*C12Q 1/68* (2018.01)
*C12Q 1/6883* (2018.01)
*G01N 33/68* (2006.01)

(56) References Cited

OTHER PUBLICATIONS

Brock et al. (Circulation Research, 2009 vol. 104:1184-1191).*
Hung et al. (Abstract, Respirology, 2013 vol. 18:151-151, PS250).*
Cai et al. (Parasites & Vectors, 2013 vol. 6:356, pp. 1-9).*
Hénique et al. (Communications orales / Néphrologie & Thérapeutique 11 (2015) 257-286, Abstract OR.04. English Translation provided by Google Translate).*
Henique et al. (Nature Communications, 2017 vol. 8:Article No. 1829, pp. 1-15).*
Cao et al. (Physiol Genomics, 2013 vol. 45:1206-1214).*

* cited by examiner

METHODS FOR THE PREVENTION AND THE TREATMENT OF EXTRACAPILLARY GLOMERULONEPHRITIS

CROSS-REFERENCE TO RELATED APPLICATIONS

This application is a continuation of U.S. patent application Ser. No. 15/112,577, filed Jul. 19, 2016 (now issued U.S. Pat. No. 9,771,584), which is the national stage of International Application PCT/EP/2015/051275, filed Jan. 22, 2015, which claims benefit of European Application 14305094.6, filed Jan. 23, 2014.

FIELD OF THE INVENTION

The present invention relates to the prevention and the treatment of extracapillary glomerulonephritis such as rapidly progressive glomerulonephritis and collapsing glomerulonephritis.

BACKGROUND OF THE INVENTION:

Extracapillary glomerulonephritis is a proliferative glomerulonephritis such as rapidly progressive glomerulonephritis and collapsing glomerulopathy. The term "extracapillary proliferation" describes proliferation of glomerular epithelial cells, namely podocytes and parietal epithelial cells.

Glomerular injury during crescentic rapidly progressive glomerulonephritis (RPGN) manifests as a proliferative histological pattern with accumulation of inflammatory cells, fibrin and proliferation of intrinsic glomerular cells in Bowman's space ("crescents") and rapid deterioration of renal function within days or months.

Rapidly progressive glomerulonephritis (RPGN) complicating necrotizing crescentic glomerulonephritis represents the most severe form of glomerular involvement and can occur in the setting of various immunological disorders, including anti-glomerular basement membrane (anti-GBM), ANCA-associated vasculitis, or immune complex diseases like lupus and infectious diseases (1, 2). Strikingly, crescent formation seems to occur downstream to inflammatory injury of the glomerulus in a way that is relatively similar whatever the causative immunological disorder. The explanation for this observation might be that the pathogenesis of RPGN is not restricted to the action of inflammatory cells and immune mediators. It has become clear that proliferation of parietal epithelial cells (3) and podocytes (4) plays a key role in crescent formation. Studies in human biopsies (5) and in a mouse model (6) demonstrated that podocytes dysregulated in RPGN, losing their original cell markers and switching to a proliferative phenotype. Convincing evidence for podocyte involvement in RPGN also came from a seminal study in a murine model where podocyte-specific deletion of the Vhl gene resulted in proliferation of podocytes, crescent formation and rapid onset of renal failure (7). The inventors recently demonstrated that the activation of the epidermal growth factor receptor (EGFR) in podocytes by de novo expression of the heparin-binding epidermal growth factor-like growth factor (HB-EGF) also plays a major role in the development of RPGN (8). Numerous proteins and signaling pathways can be activated downstream to EGFR activation, including proteins of the signal transducer and activator of transcription (STAT) family, namely STAT5 (9) and STAT3 (10). STAT3-SH2 domain can directly bind phosphorylated EGFR on tyrosine 1068 and tyrosine 1086 (11). STAT3 is a known transducer of signals from growth factors and cytokines and plays important roles in development, cell growth, prevention of apoptosis, proliferation and inflammation (12).

Accordingly, there is a need to develop new drugs that will be suitable for preventing or treating rapidly progressive glomerulonephritis (RPGN). In this way, it has been suggested that characterization of new compounds for treatment of RPGN may be highly desirable.

Collapsing glomerulopathy (CG) is a different kidney disease and is a morphologic variant of focal segmental glomerulosclerosis (FSGS) characterized by segmental and global collapse of the glomerular capillaries, marked hypertrophy and hyperplasia of podocytes, and severe tubulointerstitial disease (Albaqumi M, Barisoni L. Current views on collapsing glomerulopathy. J Am Soc Nephrol. 2008 July; 19(7):1276-81. PMID:18287560; Schwimmer J A, Markowitz G S, Valeri A, Appel G B. Collapsing glomerulopathy. Semin Nephrol. 2003 March; 23(2):209-18. PMID: 12704581). The pathogenesis of collapsing focal segmental glomerulosclerosis (FSGS) in patients not infected with HIV is not clear. As with HIV-associated nephropathy, the underlying pathogenic event appears to be a severe insult to the integrity and biology of the glomerular visceral (podocytes) and parietal epithelial cells. This damage ultimately results in cellular dedifferentiation and proliferation of these glomerular epithelial cells accompanied by a profound loss of the glomerular filtration barrier function as seen in RPGN. Activation of the STAT family, namely STAT3, has been shown in HIV (human immunodeficiency virus)-associated nephropathy, a common form of CG (He JC, Husain M, Sunamoto M, D'Agati V D, Klotman M E, Iyengar R, Klotman P E. Nef stimulates proliferation of glomerular podocytes through activation of Src-dependent Stat3 and MAPK1,2 pathways. J Clin Invest. 2004 Sep.; 114(5):643-51. PMID:15343382).

Accordingly, the characterization of new compounds for treatment of CG is highly desirable.

MicroARNs (miRNAs) are endogenous small nucleotide single-stranded non coding RNA that can disrupt protein expression by inducing translation inhibition and mRNA degradation. Recent evidence indicates that miRNA could have a pivotal role in renal disorders (13). Because STAT3 can activate the expression of various miRNAs in several proliferative disorders (14-16) and a study has found a highly conserved STAT3-binding site in the promoter region of the miR-17/92 gene in non kidney cell (17), the inventors have studied the expression of miR-92 in STAT3 modulation model.

There is no disclosure in the art of the role of miR-92a in rapidly progressive glomerulonephritis (RPGN) (or necrotizing crescentic glomerulonephritis) nor in collapsing glomerulopathy (CG), and the use of miR-92a inhibitor compounds in the prevention or treatment of RPGN and CG.

SUMMARY OF THE INVENTION:

The present invention relates to miR-92a inhibitor compound for use in the treatment of extracapillary glomerulonephritis in a subject in need thereof.

Particularly, the present invention relates to miR-92a inhibitor compound for use in the treatment of rapidly progressive glomerulonephritis (RPGN) and collapsing glomerulopathy in a subject in need thereof.

The present invention also relates to a method of identifying a subject having or at risk of having or developing extracapillary glomerulonephritis, comprising a step of measuring in a sample obtained from said subject the expression level of miR-92a.

Particularly, the present invention relates to a method of identifying a subject having or at risk of having or developing rapidly progressive glomerulonephritis (RPGN) and collapsing glomerulopathy (CG), comprising a step of measuring in a sample obtained from said subject the expression level of miR-92a.

DETAILED DESCRIPTION OF THE INVENTION

In the present invention, the inventor investigated pathological dedifferentiation of glomerular cells and microRNAs deregulation in rapidly progressive glomerulonephritis (RPGN), an extracapillary glomerulonephritis.

The inventors found that microRNA-92a (miR-92a) expression in diseased glomeruli is upregulated in experimental RPGN. The inventors demonstrated that EGFR, Interleukine-6 (IL-6) and STAT3 cascade controlled de novo expression of miR-92a in primary podocytes. Furthermore, upregulation of miR-92a glomerular expression during RPGN was found to be abrogated in vivo by EGFR kinase inhibition or podocyte specific deletion of Stat3 in mice.

The inventors also demonstrated that in vivo silencing of miR-92a using antagomiR (anti-miR-92a) strategy de-repressed CDK-inhibitor p57 expression in podocytes and prevented podocyte proliferation, glomerular demolition and renal failure. The inventors also observed that critically ill patients with RPGN had increased phospho-STAT3 and miRNA-92a glomerular expression compared to normal kidneys. and in kidney biopsies from patients diagnosed with or necrotizing crescentic glomerulonephritis of various cause, including systemic lupus erthematosus (SLE), anti-neutrophil cytoplasmic autoantibody (ANCA)-associated vasculitides and Goodpasture syndrome. miR-92a expression detected by in situ hybridization and RT-PCR in diseased glomeruli is a specific feature of necrotizing crescentic glomerulonephritis and was not found in normal kidneys and in kidney biopsies from individuals diagnosed other glomerular proteinuric diseases with no extracapillary cell proliferation such as minimal change disease, membranous nephropathy and diabetic nephropathy. It is anticipated that miR-92a is involved in any other kind of glomerular disease with extracapillary cell proliferation, including collapsing glomerulopathy.

The present invention demonstrates the implication of miR-92a in extracapillary glomerulonephritis and RPGN development with a significant pathogenic, diagnostic, and/or therapeutic implications.

Therapeutic Methods and Uses

Accordingly, the present invention relates to a miR-92a inhibitor compound for use in the prevention and treatment of extracapillary glomerulonaphritis in a subject in need thereof.

In a particular embodiment, the present invention relates to a miR-92a inhibitor compound for use in the prevention and treatment of rapidly progressive glomerulonephritis (RPGN) in a subject in need thereof.

In a particular embodiment, the present invention relates to a miR-92a inhibitor compound for use in the prevention and treatment of collapsing glomerulopathy (CG) in a subject in need thereof.

As used herein, the term "miR-92a" has its general meaning in the art and refers to the miR-92a sequence available from the data base http://microma.sanger.ac.uk/sequences/under the miRBase Accession numbers MI0000093 (hsa-mir-92a-1, SEQ ID NO: 1), MIMAT0004507 (hsa-miR-92a-1-5p, SEQ ID NO: 2), MIMAT0000092 (hsa-miR-92a-3p, SEQ ID NO: 3), MI0000094 (hsa-mir-92a-2, SEQ ID NO: 4), MIMAT0004508 (hsa-miR-92a-2-5p, SEQ ID NO: 5), MIMAT0000092 (hsa-miR-92a-3p, SEQ ID NO: 6).

As used herein, the term "subject" denotes a mammal. In a preferred embodiment of the invention, a subject according to the invention refers to any subject (preferably human) afflicted with or susceptible to be afflicted with extracapillary glomerulonephritis, particularly, rapidly progressive glomerulonephritis (RPGN) or collapsing glomerulopathy (CG).

As used herein, the term "extracapillary glomerulonephritis" is used to designate the cellular proliferation that occupies the Bowman's space,. The term "extracapillary" indicates that cell proliferation occurs outside of the capillary tuft. Extracapillary proliferation involves glomerular epithelial cells, namely podocytes and parietal epithelial cells.

As used herein, the term "rapidly progressive glomerulonephritis" or "RPGN" has its general meaning in the art and refers to crescentic rapidly progressive glomerulonephritis, the glomerular injury that manifests as a proliferative histological pattern with accumulation of inflammatory cells and proliferation of intrinsic glomerular cells in Bowman's space ("crescents") and rapid deterioration of renal function. The term "Rapidly Progressive Glomerulonephritis" relates to crescentic glomerulonephritis or necrotizing crescentic glomerulonephritis or extracapillary glomerulonephritis (Jenette J C and Thomas D B. Crescentic glomerulonephritis. Nephrol Dial Transplant. 2001;16 Suppl 6:80-2; Moeller M J, Soofi A, Hartmann I, et al. Podocytes populate cellular crescents in a murine model of inflammatory glomendonephritis. J Am Soc Nephrol 2004; 15:61-67; Tarzi R M, Cook H T, Pusey C D. Crescentic glomerulonephritis: new aspects of pathogenesis. Semin Nephrol. 2011 July; 31(4):361-8; King SK, Jeansson M, Quaggin SE et al. New insights into the pathogenesis of cellular crescents. Current Opinion in Nephrology and Hypertension 2011, 20:258-262; Robert M. Kliegman, M D, Bonita M. D. Stanton, M D, Joseph St. Gcmc, Nina Schor and Richard E. Behrman, M D. Chapter 510—Rapidly Progressive (Crescentic) Glomerulonephritis. Nelson Textbook of Pediatrics, 19th Edition—Saunders Title, ISBN: 978-1-4377-0755-7).

RPGN can be primary or secondary. Secondary forms occur in any form of severe glomerulonephritis including membranoproliferative GN, IgA nephropathy, post infectious GN, anti-neutrophil cytoplasmic autoantibody (ANCA)-associated vasculitides, and systemic lupus erythematous (SLE). RPGN can be of various etiologies including stage III and IV lupus nephritis, microscopic polyangiitis (MPA) and granulomatosis with polyangiitis (GPA).

As used herein, the term "collapsing glomerulopathy" or "CG" has its general meaning in the art anf refers to a distinct entity, so called collapsing focal segmental glomerulosclerosis (FSGS), also involves extracapillary proliferation and marked dysregulation of the quiescent podocyte phenotype (Bariety J, Nochy D, Mandet C, Jacquot C, Glotz D, Meyrier A: Podocytes undergo phenotypic changes and express macrophagic-associated markers in idiopathic collapsing glomerulopathy. Kidney Int 53 : 918-925, 1998. Srivastava T, Garola R E, Singh H K: Cell-cycle regulatory proteins in the podocyte in collapsing glomerulopathy in children. Kidney Int 70 : 529-535, 2006). Diseased podocytes exhibit a loss and gain of markers of differentiation and proliferation, respectively. Recent studies indicate that parietal epithelial cells also may be recruited into the viscerally located proliferative lesion (Dijkman H B, Weening J J, Smeets B, Verrijp K C, van Kuppevelt T H, Assmann K K, Steenbergen E J, Wetzels J: Proliferating cells in HIV and pamidronate-associated collapsing focal segmental glomerulosclerosis are parietal epithelial cells. Kidney Int 70 : 338-344, 2006).

Collapsing glomerulopathy (CG) can be primary or secondary (Albaqumi M, Barisoni L. Current views on collapsing glomerulopathy. J Am Soc Nephrol. 2008 July; 19(7): 1276-81. PMID:18287560). Secondary forms can be associated to HIV infection or other viral infections (such as hepatitis C virus infection, and parvovirus), drug addiction, pamidronate, systemic lupus erythematosus-like disorder and multiple myeloma or can be favored by genetic background.

As used herein, the term "miR-92a inhibitor compound" refers to any compound able to prevent the action of miR-92a. The miR-92a inhibitor compound of the present invention is a compound that inhibits or reduces the activity of miR-92a. However, decreasing and/or reducing the activity of miR-92a can also be obtained by inhibiting miR-92a expression. The term "inhibiting miR-92a expression" means that the production of miR-92a in the podocytes after treatment is less than the amount produced prior to treatment. One skilled in the art can readily determine whether miR-92a expression has been inhibited in a kidney or podocytes, using for example the techniques for determining miRNA transcript level.

In a particular embodiment, miR-92a inhibitor compound of the invention is a compound such as nucleic acid that hybridizes with miR-92a or having sequence complementarity to that of miR-92a. In a particular embodiment, miR-92a inhibitor compound of the invention is a compound such as nucleic acid having at least 80%, 85%, 90%, 95%, 96%, 97%, 98%, 99% or 100% sequence complementarity to that of miR-92a.

Suitable miR-92a inhibitor compounds include double-stranded RNA (such as short- or small-interfering RNA or "siRNA"), antagomirs, antisense nucleic acids, and enzymatic RNA molecules such as ribozymes. Each of these compounds can be targeted to a given miRNA and destroy or induce the destruction of the target miRNA. For example, expression of a given miRNA can be inhibited by inducing RNA interference of the miRNA with an isolated double-stranded RNA ("dsRNA") molecule which has at least 90%, for example 95%, 96%, 97%, 98%, 99% or 100%, sequence homology with at least a portion of the miRNA. In a preferred embodiment, the dsRNA molecule is a "short or small interfering RNA" or "siRNA".

siRNA useful in the present methods comprise short double-stranded RNA from about 17 nucleotides to about 29 nucleotides in length, preferably from about 19 to about 25 nucleotides in length. The siRNA comprise a sense RNA strand and a complementary antisense RNA strand annealed together by standard Watson-Crick base-pairing interactions (hereinafter "base-paired"). The sense strand comprises a nucleic acid sequence which is substantially identical to a nucleic acid sequence contained within the target miRNA.

As used herein, a nucleic acid sequence in a siRNA which is "substantially identical" to a target sequence contained within the target mRNA is a nucleic acid sequence that is identical to the target sequence, or that differs from the target sequence by one or two nucleotides. The sense and antisense strands of the siRNA can comprise two complementary, single-stranded RNA molecules, or can comprise a single molecule in which two complementary portions are base-paired and are covalently linked by a single-stranded "hairpin" area. The siRNA can also be altered RNA that differs from naturally-occurring RNA by the addition, deletion, substitution and/or alteration of one or more nucleotides. Such alterations can include addition of non-nucleotide material, such as to the end(s) of the siRNA or to one or more internal nucleotides of the siRNA, or modifications that make the siRNA resistant to nuclease digestion, or the substitution of one or more nucleotides in the siRNA with deoxyribonucleotides.

One or both strands of the siRNA can also comprise a 3' overhang. As used herein, a "3' overhang" refers to at least one unpaired nucleotide extending from the 3'-end of a duplexed RNA strand. Thus, in one embodiment, the siRNA comprises at least one 3' overhang of 1 to about 6 nucleotides (which includes ribonucleotides or deoxyribonucleotides) in length, preferably from 1 to about 5 nucleotides in length, more preferably from 1 to about 4 nucleotides in length, and particularly preferably from about 2 to about 4 nucleotides in length. In a preferred embodiment, the 3' overhang is present on both strands of the siRNA, and is 2 nucleotides in length. For example, each strand of the siRNA can comprise Y overhangs of dithymidylic acid ("TT") or diuridylic acid ("uu").

The siRNA can be produced chemically or biologically, or can be expressed from a recombinant plasmid or viral vector, as described above. Exemplary methods for producing and testing dsRNA or siRNA molecules are described in U.S. published patent application 2002/0173478 to Gewirtz and in U.S. published patent application 2004/0018176 to Reich et al., the entire disclosures of which are herein incorporated by reference.

Expression of a given miRNA can also be inhibited by an antisense nucleic acid. As used herein, an "antisense nucleic acid" refers to a nucleic acid molecule that binds to target RNA by means of RNA-RNA or RNA-DNA or RNA-peptide nucleic acid interactions, which alters the activity of the target RNA. Antisense nucleic acids suitable for use in the present methods are single-stranded nucleic acids (e.g., RNA, DNA, RNA-DNA chimeras, PNA) that generally comprise a nucleic acid sequence complementary to a contiguous nucleic acid sequence in a miRNA. Preferably, the antisense nucleic acid comprises a nucleic acid sequence that is 50-100% complementary, more preferably 75-100% complementary, and most preferably 95-100% complementary to a contiguous nucleic acid sequence in an miRNA. Nucleic acid sequences for the miRNAs are provided in Table A. Without wishing to be bound by any theory, it is believed that the antisense nucleic acids activate RNase H or some other cellular nuclease that digests the miRNA/antisense nucleic acid duplex.

In a preferred embodiment the inhibitor is an antagomir and/or an antisense oligonucleotide.

The term "antagomir" or "antagomiR-92a" as used herein refers to a chemically engineered small RNA that is used to silence miR-92a. The antagomir is complementary to the specific miRNA target with either mis-pairing or some sort of base modification. Antagomirs may also include some sort of modification to make them more resistant to degradation. In a preferred embodiment the antagomir is a chemically engineered cholesterol-conjugated single-stranded RNA analogue.

Inhibition of miR-92a can also be achieved with antisense 2'-O-methyl (2'-O-Me) oligoribonucleotides, 2'-O-methoxyethyl (2'-O-MOE), phosphorothioates, locked nucleic acid (LNA), morpholino oligomers or by use of lentivirally or adenovirally expressed antagomirs (Stenvang and Kauppinen (2008), Expert Opin. Biol. Ther. 8(1):59-81). Furthermore, MOE (2'-O-methoxyethyt phosphorothioate) or LNA (locked nucleic acid (LNA) phosphorothioate chemistry)-modification of single-stranded RNA analogous can be used to inhibit miRNA activity.

Antisense nucleic acids can also contain modifications of the nucleic acid backbone or of the sugar and base moieties (or their equivalent) to enhance target specificity, nuclease resistance, delivery or other properties related to efficacy of the molecule. Such modifications include cholesterol moieties, duplex intercalators such as acridine or the inclusion of one or more nuclease-resistant groups.

Antisense nucleic acids can be produced chemically or biologically, or can be expressed from a recombinant plasmid or viral vector, as described below. Exemplary methods for producing and testing are within the skill in the art; see, e.g., Stein and Cheng (1993), Science 261:1004 and U.S. Pat. No. 5,849,902 to Woolf et al., the entire disclosures of which are herein incorporated by reference.

Expression of a given miRNA can also be inhibited by an enzymatic nucleic acid. As used herein, an "enzymatic nucleic acid" refers to a nucleic acid comprising a substrate binding region that has complementarity to a contiguous nucleic acid sequence of a miRNA, and which is able to specifically cleave the miRNA. Preferably, the enzymatic nucleic acid substrate binding region is 50-100% complementary, more preferably 75-100% complementary, and most preferably 95-100% complementary to a contiguous nucleic acid sequence in a miRNA. The enzymatic nucleic acids can also comprise modifications at the base, sugar, and/or phosphate groups. An exemplary enzymatic nucleic acid for use in the present methods is a ribozyme.

The enzymatic nucleic acids can be produced chemically or biologically, or can be expressed from a recombinant plasmid or viral vector, as described below. Exemplary methods for producing and testing dsRNA or siRNA molecules are described in Werner and Uhlenbeck (1995), Nucl. Acids Res. 23:2092-96; Hammann et al. (1999), Antisense and Nucleic Acid Drug Dev. 9:25-31; and U.S. Pat. No. 4,987,071 to Cech et al, the entire disclosures of which are herein incorporated by reference.

The miR-92a inhibitor compound of the invention can be obtained using a number of standard techniques. For example the miR-92a inhibitor compound of the invention can be chemically synthesized or recombinantly produced using methods known in the art. Typically, miR-92a inhibitor compound of the invention are chemically synthesized using appropriately protected ribonucleoside phosphoramidites and a conventional DNA/RNA synthesizer. Commercial suppliers of synthetic RNA molecules or synthesis reagents include, e.g., Proligo (Hamburg, Germany), Dharmacon Research (Lafayette, Colo., USA), Pierce Chemical (part of Perbio Science, Rockford, 111., USA), Glen Research (Sterling, Va., USA), ChemGenes (Ashland, Mass., USA) and Cruachem (Glasgow, UK).

In some embodiments, of the invention, a synthetic miR-92a inhibitor compound of the invention contains one or more design elements. These design elements include, but are not limited to: (i) a replacement group for the phosphate or hydroxyl of the nucleotide at the 5' terminus of the complementary region; (ii) one or more sugar modifications. In certain embodiments, a synthetic miR-92a inhibitor compound of the invention has a nucleotide at its 5' end of the complementary region in which the phosphate and/or hydroxyl group has been replaced with another chemical group (referred to as the "replacement design"). In some cases, the phosphate group is replaced, while in others, the hydroxyl group has been replaced. In particular embodiments, the replacement group is biotin, an amine group, a lower alkylamine group. an acetyl group, 2'O-Me (2'oxygenmethyl), DMTO (4,4'-dimethoxytrityl with oxygen), fluorescein, a thiol, or acridine, though other replacement groups are well known to those of skill in the art and can be used as well. In particular embodiments, the sugar modification is a 2'O-Me modification. In further embodiments, there is one or more sugar modifications in the first or last 2 to 4 residues of the complementary region or the first or last 4 to 6 residues of the complementary region.

In a particular embodiment, the miR-92a inhibitor compound of the invention is resistant to degradation by nucleases. One skilled in the art can readily synthesize nucleic acids which are nuclease resistant, for example by incorporating one or more ribonucleotides that are modified at the 2'-position into the miRNAs. Suitable 2'-modified ribonucleotides include those modified at the 2'-position with fluoro, amino, alkyl, alkoxy, and O-allyl.

The present invention also relates to a vector comprising a miR-92a inhibitor compound according to the invention for use in the prevention and treatment of extracapillary glomerulonephritis, rapidly progressive glomerulonephritis (RPGN) and collapsing glomerulopathy (CG).

Alternatively, the miR-92a inhibitor compound of the invention can be expressed from recombinant circular or linear DNA plasmids using any suitable promoter. Suitable promoters for expressing RNA from a plasmid include, e.g., the U6 or HI RNA pol III promoter sequences, or the cytomegalovirus promoters. Selection of other suitable promoters is within the skill in the art. The recombinant plasmids of the invention can also comprise inducible or regulatable promoters for expression of the miR-92a inhibitor compound of the invention in podocytes.

The miR-92a inhibitor compound of the invention that is expressed from recombinant plasmids can be isolated from cultured cell expression systems by standard techniques. The miR-92a inhibitor compound of the invention which is expressed from recombinant plasmids can also be delivered to, and expressed directly in, the podocytes. The use of recombinant plasmids to deliver the miR-92a inhibitor compound of the invention to podocytes is discussed in more detail below.

The miR-92a inhibitor compound of the invention can be expressed from a separate recombinant plasmid, or can be expressed from a unique recombinant plasmid. Preferably, the miR-92a inhibitor compound of the invention is expressed as the nucleic acid precursor molecules from a single plasmid, and the precursor molecules are processed into the functional miR-92a inhibitor compound by a suitable processing system, including processing systems extant within podocytes. Other suitable processing systems include, e.g., the in vitro Drosophila cell lysate system as described in U.S. published application 2002/0086356 to Tuschl et al. and the E. coli RNAse III system described in U.S. published patent application 2004/0014113 to Yang et al., the entire disclosures of which are herein incorporated by reference.

Selection of plasmids suitable for expressing the miR-92a inhibitor compound of the invention, methods for inserting nucleic acid sequences into the plasmid to express the gene products, and methods of delivering the recombinant plasmid to the cells of interest are within the skill in the art. See, for example, Zeng et al. (2002), Molecular Cell 9:1327-

1333; Tuschl (2002), Nat. Biotechnol, 20:446-448; Brummelkamp et al. (2002), Science 296:550-553; Miyagishi et al. (2002), Nat. Biotechnol. 20:497-500; Paddison et al. (2002), Genes Dev. 16:948-958; Lee et al. (2002), Nat. Biotechnol. 20:500-505; and Paul et al. (2002), Nat. Biotechnol. 20:505-508, the entire disclosures of which are herein incorporated by reference.

In one embodiment, a plasmid expressing the miR-92a inhibitor compound of the invention comprises a sequence encoding a miR-92a inhibitor compound precursor under the control of the CMV intermediate early promoter. As used herein, "under the control" of a promoter means that the nucleic acid sequences are located 3' of the promoter, so that the promoter can initiate transcription of the miR-92a inhibitor compound coding sequences.

The miR-92a inhibitor compound of the invention can also be expressed from recombinant viral vectors. It is contemplated that the miR-92a inhibitor compound of the invention can be expressed from separate recombinant viral vectors, or from a unique viral vector. The miR-92a inhibitor compound expressed from the recombinant viral vectors can either be isolated from cultured cell expression systems by standard techniques, or can be expressed directly in podocytes. The use of recombinant viral vectors to deliver the miR-92a inhibitor compound to podocytes is discussed in more detail below.

The recombinant viral vectors of the invention comprise sequences encoding the miR-92a inhibitor compound of the invention and any suitable promoter for expressing the miR-92a inhibitor compound sequences. Suitable promoters include, for example, the U6 or HI RNA pol 111 promoter sequences, or the cytomegalovirus promoters. Selection of other suitable promoters is within the skill in the art. The recombinant viral vectors of the invention can also comprise inducible or regulatable promoters for expression of the miR-92a inhibitor compound in podocytes.

Any viral vector capable of accepting the coding sequences for the miR-92a inhibitor compound of the invention can be used; for example, vectors derived from adenovirus (AV); adenoassociated virus (AAV); retroviruses (e.g., lentiviruses (LV), Rhabdoviruses, murine leukemia virus); herpes virus, and the like. The tropism of the viral vectors can be modified by pseudotyping the vectors with envelope proteins or other surface antigens from other viruses, or by substituting different viral capsid proteins, as appropriate. For example, lentiviral vectors of the invention can be pseudotyped with surface proteins from vesicular stomatitis virus (VSV), rabies, Ebola, Mokola, and the like. AAV vectors of the invention can be made to target different cells by engineering the vectors to express different capsid protein serotypes. For example, an AAV vector expressing a serotype 2 capsid on a serotype 2 genome is called AAV 2/2. This serotype 2 capsid gene in the AAV 2/2 vector can be replaced by a serotype 5 capsid gene to produce an AAV $^2/_5$ vector. Techniques for constructing AAV vectors which express different capsid protein serotypes are within the skill in the art; see. e.g., Rabinowitz J. E. et al. (2002), J Virol 76:791801, the entire disclosure of which is herein incorporated by reference.

Selection of recombinant viral vectors suitable for use in the invention, methods for inserting nucleic acid sequences for expressing said miR-92a inhibitor compound of the invention into the vector, methods of delivering the viral vector to the cells of interest, and recovery of the expressed miR-92a inhibitor compound products are within the skill in the art. See, for example, Dornburg (1995), Gene Therap. 2:301-310; Eglitis (1988), Biotechniques 6:608-614; Miller (1990), Hum. Gene Therap. 1:5-14; and Anderson (1998), Nature 392:25-30, the entire disclosures of which are herein incorporated by reference.

Preferred viral vectors are those derived from AV and AAV. A suitable AV vector for expressing the miR-92a inhibitor compound of the invention, a method for constructing the recombinant AV vector, and a method for delivering the vector into target cells, are described in Xia et al. (2002), Nat. Biotech. 20:1006-1010, the entire disclosure of which is herein incorporated by reference. Suitable AAV vectors for expressing the miR-92a inhibitor compound of the invention, methods for constructing the recombinant AAV vector, and methods for delivering the vectors into target cells are described in Samulski et al. (1987), J. Virol. 61:3096-3101; Fisher et al. (1996), J. Virol., 70:520-532; Samulski et al. (1989), J. Virol. 63:3822-3826; U.S. Pat. No. 5,252,479; U.S. Pat. No. 5,139,941; International Patent Application No. WO 94/13788; and International Patent Application No. WO 93/24641, the entire disclosures of which are herein incorporated by reference. Preferably, the miR-92a inhibitor compound of the invention is expressed from a single recombinant AAV vector comprising the CMV intermediate early promoter.

In one embodiment, a recombinant AAV viral vector of the invention comprises a nucleic acid sequence encoding a miR-92a inhibitor compound precursor in operable connection with a polyT termination sequence under the control of a human U6 RNA promoter. As used herein, "in operable connection with a polyT termination sequence" means that the nucleic acid sequences encoding the sense or antisense strands are immediately adjacent to the polyT termination signal in the 5' direction. During transcription of the miR-92a inhibitor compound sequences from the vector, the polyT termination signals act to terminate transcription.

The miR-92a inhibitor compound can be administered to a subject by any means suitable for delivering these compounds to kidney or podocytes of the subject. For example, the miR-92a inhibitor compound can be administered by methods suitable to transfect cells of the subject with these compounds, or with nucleic acids comprising sequences encoding these compounds. Preferably, the cells are transfected with a plasmid or viral vector comprising sequences encoding at least one miR-92a inhibitor compound.

The miR-92a inhibitor compound can be administered to a subject by any suitable enteral or parenteral administration route. Suitable enteral administration routes for the present methods include, e.g., oral, rectal, or intranasal delivery. Suitable parenteral administration routes include, e.g., intravascular administration (e.g., intravenous bolus injection, intravenous infusion, intra-arterial bolus injection, intra-arterial infusion and catheter instillation into the vasculature); peri- and intra-tissue injection (e.g., intra-retinal injection, or subretinal injection); subcutaneous injection or deposition, including subcutaneous infusion (such as by osmotic pumps); direct application to the tissue of interest, for example by a catheter or other placement device (e.g., a retinal pellet or a suppository or an implant comprising a porous, non-porous, or gelatinous material); and inhalation. PrefelTed administration routes are injection, infusion and direct injection into the kidneey tissue.

In the present methods, a miR-92a inhibitor compound can be administered to the subject either as naked RNA, in combination with a delivery reagent, or as a nucleic acid (e.g., a recombinant plasmid or viral vector) comprising sequences that express the miR-92a inhibitor compound. Suitable delivery reagents include, e.g, the Minis Transit TKO lipophilic reagent; lipofectin; lipofectamine; cellfectin; polycations (e.g., polylysine), and liposomes.

Recombinant plasmids and viral vectors comprising sequences that express the miR-92a inhibitor compounds, and techniques for delivering such plasmids and vectors to podocytes, are discussed above.

In a preferred embodiment, liposomes are used to deliver a miR-92a inhibitor compound (or nucleic acids comprising sequences encoding them) to a subject. Liposomes can also increase the blood half-life of the gene products or nucleic acids. Liposomes suitable for use in the invention can be formed from standard vesicle-forming lipids, which generally include neutral or negatively charged phospholipids and a sterol, such as cholesterol. The selection of lipids is generally guided by consideration of factors such as the desired liposome size and half-life of the Liposomes in the blood stream.

A variety of methods are known for preparing liposomes, for example, as described in Szoka et al. (1980), Ann. Rev. Biophys. Bioeng. 9:467; and U.S. Pat. Nos. 4,235,871, 4,501,728, 4,837,028, and 5,019,369, the entire disclosures of which are herein incorporated by reference. The liposomes for use in the present methods can comprise a ligand molecule that targets the liposome to podocytes. Ligands which bind to receptors prevalent in podocytes, such as monoclonal antibodies that bind to podocytes antigens, arc preferred. The liposomes for use in the present methods can also be modified so as to avoid clearance by the mononuclear macrophage system ("MMS") and reticuloendothelial system ("RES"). Such modified liposomes have opsonization-inhibition moieties on the surface or incorporated into the Liposome structure. In a particularly preferred embodiment, a Liposome of the invention can comprise both opsonization-inhibition moieties and a ligand.

Opsonization-inhibiting moieties for use in preparing the liposomes of the invention are typically large hydrophilic polymers that are bound to the liposome membrane. As used herein, an opsonization inhibiting moiety is "bound" to a liposome membrane when it is chemically or physically attached to the membrane, e.g., by the intercalation of a lipid-soluble anchor into the membrane itself, or by binding directly to active groups of membrane lipids. These opsonization-inhibiting hydrophilic polymers form a protective surface layer that significantly decreases the uptake of the liposomes by the MMS and RES; e.g., as described in U.S. Pat. No. 4,920,016, the entire disclosure of which is herein incorporated by reference. Opsonization inhibiting moieties suitable for modifying liposomes are preferably water-soluble polymers with a number-average molecular weight from about 500 to about 40,000 daltons, and more preferably from about 2,000 to about 20,000 daltons. Such polymers include polyethylene glycol (PEG) or polypropylene glycol (PPG) derivatives; e.g., methoxy PEG or PPG, and PEG or PPG stearate; synthetic polymers such as polyacrylamide or poly N-vinyl pyrrolidone; linear, branched, or dendrimeric polyamidoamines; polyacrylic acids; polyalcohols, e.g., polyvinylalcohot and polyxylitol to which carboxylic or amino groups are chemically linked, as well as gangliosides, such as ganglioside GM1. Copolymers of PEG, methoxy PEG, or methoxy PPG, or derivatives thereof, are also suitable. In addition, the opsonization inhibiting polymer can be a block copolymer of PEG and either a polyamino acid, polysaccharide, polyamidoamine, polyethyleneamine, or polynucleotide. The opsonization inhibiting polymers can also be natural polysaccharides containing amino acids or carboxylic acids, e.g., galacturonic acid, glucuronic acid, mannuronic acid, hyaluronic acid, pectic acid, neuraminic acid, alginic acid, carrageenan; animated polysaccharides or oligosaccharides (linear or branched); or carboxylated polysaccharides or oligosaccharides, e.g., reacted with derivatives of carbonic acids with resultant linking of carboxylic groups. Preferably, the opsonization-inhibiting moiety is a PEG, PPG, or derivatives thereof. Liposomes modified with PEG or PEG-derivatives are sometimes called "PEGylated liposomes".

The opsonization inhibiting moiety can be bound to the liposome membrane by any one of numerous well-known techniques. For example, an N-hydroxysuccinimide ester of PEG can be bound to a phosphatidyl-ethanolamine lipid-soluble anchor, and then bound to a membrane. Similarly, a dextran polymer can be derivatized with a stearylamine lipid-soluble anchor via reductive animation using Na(CN)BH3 and a solvent mixture, such as tetrahydrofuran and water in a 30:12 ratio at 60° C.

Liposomes modified with opsonization-inhibition moieties remain in the circulation much longer than unmodified liposomes. For this reason, such liposomes are sometimes called "stealth" liposomes. Stealth liposomes are known to accumulate in tissues fed by porous or "leaky" microvasculature. Thus, tissue characterized by such microvasculature defects will efficiently accumulate these liposomes; see Gabizon, et al. (1988), Proc. Natl. Acad. Sci., USA, 18:6949-53. In addition, the reduced uptake by the RES lowers the toxicity of stealth liposomes by preventing significant accumulation of the liposomes in the liver and spleen. Thus, liposomes that are modified with opsonization-inhibition moieties are particularly suited to deliver the miR-92a inhibitor compounds (or nucleic acids comprising sequences encoding them) to podocytes.

One skilled in the art can readily determine a therapeutically effective amount of said compound to be administered to a given subject, by taking into account factors such as the size and weight of the subject; the extent of disease penetration; the age, health and sex of the subject; the route of administration; and whether the administration is regional or systemic. An effective amount of said compound can be based on the approximate or estimated body weight of a subject to be treated. Preferably, such effective amounts are administered parenterally or enterally, as described herein. For example, an effective amount of the compound is administered to a subject can range from about 5-10000 micrograms/kg of body weight, and is preferably between about 5-3000 micrograms/kg of body weight, and is preferably between about 700-1000 micrograms/kg of body weight, and is more preferably greater than about 1000 micrograms/kg of body weight. One skilled in the art can also readily determine an appropriate dosage regimen for the administration of the compound to a given subject. For example, the compound can be administered to the subject once (e.g., as a single injection or deposition).

In another embodiment, the present invention relates to a method of preventing or treating extracapillary glomerulonephritis in a subject in need thereof, comprising the step of administering to said subject a miR-92a inhibitor compound.

Pharmaceutical Compositions

The miR-92a inhibitor compound of the invention may be used or prepared in a pharmaceutical composition.

In one embodiment, the invention relates to a pharmaceutical composition comprising a miR-92a inhibitor compound and a pharmaceutical acceptable carrier for use in the prevention and treatment of extracapillary glomerulonephritis in a subject in need thereof.

In a particular embodiment, the invention relates to a pharmaceutical composition comprising a miR-92a inhibitor compound and a pharmaceutical acceptable carrier for use in the prevention and treatment of rapidly progressive glomerulonephritis (RPGN) and collapsing glomerulopathy (CG) in a subject in need thereof.

The miR-92a inhibitor compounds of the invention are preferably formulated as pharmaceutical compositions, prior to administering to a patient, according to techniques known in the art. Pharmaceutical compositions of the present invention are characterized as being at least sterile and pyrogen-free. As used herein, "pharmaceutical formulations" include formulations for human and veterinary use. Methods for preparing pharmaceutical compositions of the invention are within the skill in the art, for example as described in Remington's Pharmaceutical Science, 17th ed., Mack Publishing Company, Easton, Pa. (1985), the entire disclosure of which is herein incorporated by reference.

The present pharmaceutical formulations comprise miR-92a inhibitor compound (e.g., 0.1 to 90% by weight), or a physiologically acceptable salt thereof, mixed with a pharmaceutically-acceptable carrier. The pharmaceutical formulations of the invention can also comprise miR-92a inhibitor compound which are encapsulated by liposomes and a pharmaceutically-acceptable carrier. Preferred pharmaceutically-acceptable carriers are water, buffered water, normal saline, 0.4% saline, 0.3% glycine, hyaluronic acid and the like.

Pharmaceutical compositions of the invention can also comprise conventional pharmaceutical excipients and/or additives. Suitable pharmaceutical excipients include stabilizers, antioxidants, osmolality adjusting agents, buffers, and pH adjusting agents. Suitable additives include, e.g., physiologically biocompatible buffers (e.g., tromethamine hydrochloride), additions of chelants (such as, for example, DTPA or DTPA-bisamide) or calcium chelate complexes (such as, for example, calcium DTPA, CaNaDTPA-bisamide), or, optionally, additions of calcium or sodium salts (for example, calcium chloride, calcium ascorbate, calcium gluconate or calcium lactate). Pharmaceutical compositions of the invention can be packaged for use in liquid form, or can be lyophilized.

For solid pharmaceutical compositions of the invention, conventional nontoxic solid pharmaceutically acceptable carriers can be used; for example, pharmaceutical grades of mannitol, lactose, starch, magnesium stearate, sodium saccharin, talcum, cellulose, glucose, sucrose, magnesium carbonate, and the like.

For example, a solid pharmaceutical composition for oral administration can comprise any of the carriers and excipients listed above and 10-95%, preferably 25%-75%, of the miR-92a inhibitor compound. A pharmaceutical composition for aerosol (inhalational) administration can comprise 0.01-20% by weight, preferably 1%-10% by weight, of the miR-92a inhibitor compound encapsulated in a liposome as described above, and a propellant. A carrier can also be included as desired; e.g., lecithin for intranasal delivery.

Pharmaceutical compositions of the invention may include any further agent which is used in the prevention or treatment of extracapillary glomerulonephritis, rapidly progressive glomerulonephritis (RPGN) or collapsing glomerulopathy (CG).

For example, the anti-RPGN therapy may include cyclophosphamide, plasmapheresis, anti-CD20 antibody, mycophenolate mofetil and corticosteroids such as methylprednisolone or prednisone.

For example, the anti-CG therapy may include steroids or cyclosporine, angiotensin converting enzyme inhibitors and/or angiotensin it receptor blockers, anti-HIV therapy, lipid lowering agents and mycophenolate mofetil.

In one embodiment, said additional active agents may be contained in the same composition or administrated separately.

In another embodiment, the pharmaceutical composition of the invention relates to combined preparation for simultaneous, separate or sequential use in the prevention and treatment of rapidly progressive glomerulonephritis (RPGN).

The invention also provides kits comprising the miR-92a inhibitor compound of the invention. Kits containing the miR-92a inhibitor compound of the invention find use in therapeutic methods.

Diagnostics Methods:

A further aspect of the invention relates to a method of identifying a subject having or at risk of having or developing extracapillary glomerulonephritis, comprising a step of measuring in a sample obtained from said subject the expression level of miR-92a.

In a particular embodiment, the present invention relates to a method of identifying a subject having or at risk of having or developing rapidly progressive glomerulonephritis (RPGN), comprising a step of measuring in a sample obtained from said subject the expression level of miR-92a.

In a particular embodiment, the present invention relates to a method of identifying a subject having or at risk of having or developing collapsing glomerulopathy (CG), comprising a step of measuring in a sample obtained from said subject the expression level of miR-92a.

The method of the invention may further comprise a step consisting of comparing the expression level of miR-92a in the sample with a control, wherein detecting differential in the expression level of the miR-92a between the sample and the control is indicative of subject having or at risk of having or developing an extracapillary glomerulonephritis, a rapidly progressive glomerulonephritis (RPGN) or a collapsing glomerulopathy (CG).

In one embodiment, the control may consist in sample associated with a healthy subject not afflicted with extracapillary glomerulonephritis, not afflicted with rapidly progressive glomerulonephritis (RPGN) and not afflicted with collapsing glomerulopathy (CG) as a negative control. Accordingly, a higher expression level of miR-92a in the sample than the control is indicative of a subject having or at risk of having or developing an extracapillary glomerulonephritis, a rapidly progressive glomerulonephritis (RPGN) or a collapsing glomerulopathy (CG), and a lower or equal expression level of miR-92a in the sample than the control is indicative of a subject not having or not at risk of having or developing an extracapillary glomerulonephritis, a rapidly progressive glomerulonephritis (RPGN) or a collapsing glomerulopathy (CG).

In another embodiment, the control may consist in sample associated with a subject afflicted with extracapillary glomerulonephritis, rapidly progressive glomerulonephritis (RPGN) or collapsing glomerulopathy (CG) as a positive control. Accordingly, a higher or equal expression level of miR-92a in the sample than the control is indicative of a subject having or at risk of having or developing an extracapillary glomerulonephritis, a rapidly progressive glomerulonephritis (RPGN) or a collapsing glomerulopathy (CG), and a lower expression level of miR-92a in the sample than the control is indicative of a subject not having or not at risk of having or developing an extracapillary glomerulonephritis, a rapidly progressive glomerulonephritis (RPGN) or a collapsing glomerulopathy (CG).

According to the invention, measuring the expression level of the miR-92a of the invention in the sample obtained from the subject can be performed by a variety of techniques.

For example the nucleic acid contained in the samples (e.g., cell or tissue prepared from the subject) is first extracted according to standard methods, for example using lytic enzymes or chemical solutions or extracted by nucleic-acid-binding resins following the manufacturer's instructions. Conventional methods and reagents for isolating RNA from a sample comprise High Pure miRNA Isolation Kit (Roche), Trizol (lnvitrogen), Guanidinium thiocyanate-phenol-chloroform extraction, PureLink™ miRNA isolation kit (Invitrogen), PureLink Micro-to-Midi Total RNA Purification System (invitrogcn), RNcasy kit (Qiagcn), miRNeasy kit (Qiagen), Oligotex kit (Qiagen), phenol extraction, phenol-chloroform extraction, TCA/acetone precipitation, ethanol precipitation, Column purification, Silica gel membrane purification, PureYield™ RNA Midiprep (Promega), PolyATtract System 1000 (Promega), Maxwell® 16 System (Promega), SV Total RNA Isolation (Promega), geneMAG-RNA/DNA kit (Chemicell), TRI Reagent® (Ambion), RNAqueous Kit (Ambion), ToTALLY RNA™ Kit (Ambion), Poly(A)Purist™ Kit (Ambion) and any other methods, commercially available or not, known to the skilled person.

The expression level of miR-92a in the sample may be determined by any suitable method. Any reliable method for measuring the level or amount of miRNA in a sample may be used. Generally, miR-92a can be detected and quantified from a sample (including fractions thereof), such as samples of isolated RNA by various methods known for mRNA, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoString analysis, Northern Blot analysis, branched DNA (bDNA) signal amplification, in situ hybridization, etc.), and sequencing-based methods (e.g., next-generation sequencing methods, for example, using the IIIumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In some embodiments, the expression level of miRNA is measured during the amplification process. In some embodiments, the expression level of miRNA is not amplified prior to measurement. Some exemplary methods suitable for determining the expression level of miRNA in a sample are described in greater hereinafter. These methods are provided by way of illustration only, and it will be apparent to a skilled person that other suitable methods may likewise be used.

Many amplification-based methods exist for detecting the expression level of miRNA nucleic acid sequences, including, but not limited to, PCR, RT-PCR, qPCR, and rolling circle amplification. Other amplification-based techniques include, for example, ligase chain reaction (LCR), multiplex ligatable probe amplification, in vitro transcription (IVT), strand displacement amplification (SDA), transcription-mediated amplification (TMA), nucleic acid sequence based amplification (NASBA), RNA (Eberwine) amplification, and other methods that are known to persons skilled in the art. A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence. In some embodiments, custom qRT-PCR assays can be developed for determination of miRNA levels. Custom qRT-PCR assays to measure miRNAs in a sample can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in the samples. Amplification curves may optionally be checked to verify that Ct values arc assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the $2(-\Delta\Delta C(T))$ Method, as described by Livak et ah, Analysis of relative gene expression data using real-time quantitative PCR and the $2(-\Delta\Delta C(T))$ Method. Methods (2001) December;25(4):402-8.

Rolling circle amplification is a DNA-polymerase driven reaction that can replicate circularized oligonucleotide probes with either linear or geometric kinetics under isothermal conditions (see, for example, Lizardi et al., Nat. Gen. (1998) 19(3):225-232; Gusev et al, Am. J. Pathol. (2001) 159(1):63-69: Nallur et al, Nucleic Acids Res. (2001) 29(23):E118). In the presence of two primers, one hybridizing to the (+) strand of DNA, and the other hybridizing to the (−) strand, a complex pattern of strand displacement results in the generation of over $10^9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations (see, for example, Cheng et al., Angew Chem. Int. Ed. Engl. (2009) 48(18):3268-72; Neubacher et al, Chembiochem. (2009) 10(8): 1289-91).

miRNAs quantification method may be performed by using stem-loop primers for reverse transcription (RT) followed by a real-time TaqMan® probe. Typically, said method comprises a first step wherein the stem-loop primers are annealed to miRNA targets and extended in the presence of reverse transcriptase. Then miRNA-specific forward primer, TaqMan® probe, and reverse primer are used for PCR reactions. Quantitation of miRNAs is estimated based on measured CT values.

Many miRNA quantification assays are commercially available from Qiagen (S. A. Courtabocuf, France), Exiqon (Vedback Denmark) or Applied Biosystems (Foster City, USA).

Expression level of miR-92a may be expressed as absolute expression level or normalized expression level. Typically, expression levels are normalized by correcting the absolute expression level of miR-92a by comparing its expression to the expression of a mRNA that is not a relevant for determining patient having or at risk of having or developing a rapidly progressive glomerulonephritis (RPGN), e.g., a housekeeping mRNA that is constitutively expressed. Suitable mRNA for normalization include housekeeping mRNAs such as the U6, U24, U48 and S18. This normalization allows the comparison of the expression level in one sample, e.g., a subject sample, to another sample, or between samples from different sources.

Nucleic acids exhibiting sequence complementarity or homology to the miRNA of interest herein find utility as hybridization probes or amplification primers. It is understood that such nucleic acids need not be identical, but are typically at least about 80% identical to the homologous region of comparable size, more preferably 85% identical and even more preferably 90-95% identical. In certain embodiments, it will be advantageous to use nucleic acids in combination with appropriate means, such as a detectable label, for detecting hybridization. A wide variety of appropriate indicators are known in the art including, fluorescent, radioactive, enzymatic or other ligands (c. g. avidin/biotin).

The probes and primers are "specific" to the miR-92a they hybridize to, i.e. they preferably hybridize under high stringency hybridization conditions (corresponding to the highest melting temperature Tm, e.g., 50% formamide, 5× or 6× SCC. SCC is a 0.15 M NaCl, 0.015 M Na-citrate).

miRNA may be detected using hybridization-based methods, including but not limited to hybridization arrays (e.g., microarrays), NanoString analysis, Northern Blot analysis, branched DNA (bDNA) signal amplification, and in situ hybridization.

Microarrays can be used to measure the expression level of miR-92a. Microarrays can be fabricated using a variety of technologies, including printing with fine-pointed pins onto glass slides, photolithography using pre-made masks, photolithography using dynamic micromirror devices, inkjet printing, or electrochemistry on microelectrode arrays. Also useful are microfluidic TaqMan Low-Density Arrays, which are based on an array of microfluidic qRT-PCR reactions, as well as related microfluidic qRT-PCR based methods. In one example of microarray detection, various oligonucleotides (e.g., 200+5'-amino-modified-C6 oligos) corresponding to human sense miRNA sequences are spotted on three-dimensional CodeLink slides (GE Health/Amersham Biosciences) at a final concentration of about 20 µM and processed according to manufacturer's recommendations. First strand cDNA synthesized from 20 µg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol. Axon B-4000 scanner and Gene-Pix Pro 4.0 software or other suitable software can be used to scan images. Non-positive spots after background subtraction, and outliers detected by the ESD procedure, are removed. The resulting signal intensity values are normalized to per-chip median values and then used to obtain geometric means and standard errors. miRNA signal can be transformed to log base 2, and a one-sample t test can be conducted. Independent hybridizations for each sample can be performed on chips with miRNA spotted multiple times to increase the robustness of the data.

Microarrays can be used for the expression profiling of miR-92a. For example. RNA can be extracted from the sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the, capture probes are affixed. The spot will then fluoresce when excited using a microarray laser scanner. The fluorescence intensity of each spot is then evaluated in terms of the number of copies of a particular miRNA, using a number of positive and negative controls and array data normalization methods, which will result in assessment of the level of expression of a particular miRNA. Total RNA containing the miRNA extracted from the sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA. Several types of microarrays can be employed including, but not limited to, spotted oligonucleotide microarrays, pre-fabricated oligonucleotide microarrays or spotted long oligonucleotide arrays.

Accordingly, the nucleic acid probes include one or more labels, for example to permit detection of a target nucleic acid molecule using the disclosed probes. In various applications, such as in situ hybridization procedures, a nucleic acid probe includes a label (e.g., a detectable label). A "detectable label" is a molecule or material that can be used to produce a detectable signal that indicates the presence or concentration of the probe (particularly the bound or hybridized probe) in a sample. Thus, a labeled nucleic acid molecule provides an indicator of the presence or concentration of a target nucleic acid sequence (e.g., genomic target nucleic acid sequence) (to which the labeled uniquely specific nucleic acid molecule is bound or hybridized) in a sample. A label associated with one or more nucleic acid molecules (such as a probe generated by the disclosed methods) can be detected either directly or indirectly. A label can be detected by any known or yet to be discovered mechanism including absorption, emission and/or scattering of a photon (including radio frequency, microwave frequency, infrared frequency, visible frequency and ultraviolet frequency photons). Detectable labels include colored, fluorescent, phosphorescent and luminescent molecules and materials, catalysts (such as enzymes) that convert one substance into another substance to provide a detectable difference (such as by converting a colorless substance into a colored substance or vice versa, or by producing a precipitate or increasing sample turbidity), haptens that can be detected by antibody binding interactions, and paramagnetic and magnetic molecules or materials.

Particular examples of detectable labels include fluorescent molecules (or fluorochromes). Numerous fluorochromes are known to those of skill in the art, and can be selected, for example from Life Technologies (formerly Invitrogen), e.g., see, The Handbook-A Guide to Fluorescent Probes and Labeling Technologies). Examples of particular fluorophores that can be attached (for example, chemically conjugated) to a nucleic acid molecule (such as a uniquely specific binding region) are provided in U.S. Pat. No. 5,866,366 to Nazarenko et al., such as 4-acetamido-4'-isothiocyanatostilbene-2,2' disulfonic acid, acridine and derivatives such as acridine and acridine isothiocyanate, 5-(2'-aminoethyl) aminonaphthalene-1-sulfonic acid (EDANS),4-amino-N-[3 vinylsulfonyl)phenyl]naphthalimide-3,5 disulfonate (Lucifer Yellow VS), N-(4-anilino-1-naphthyl)maleimide, antl1ranilamide, Brilliant Yellow, coumarin and derivatives such as coumarin, 7-amino-4-methylcoumarin (AMC, Coumarin 120), 7-amino-4-trifluoromcthylcouluarin (Coumarin 151); cyanosinc; 4',6-diaminidino-2-phenylindole (DAPI); 5',5''dibromopyrogallol-sulfonephthalein (Bromopyrogallol Red); 7-diethylamino-3-(4'-isothiocyanatophenyl)-4-methylcoumarin; diethylenetriamine pentaacetate; 4,4'-diisothiocyanatodihydro-stilbene-2,2'-disulfonic acid; 4,4'-diisothiocyanatostilbene-2,2'-disulforlic acid; 5-[dimethylamino] naphthalene-1-sulfonyl chloride (DNS, dansyl chloride); 4-(4'-dimethylaminophenylazo)benzoic acid (DABCYL); 4-dimethylaminophenylazophenyl-4'-isothiocyanate (DABITC); eosin and derivatives such as eosin and eosin isothiocyanate; erythrosin and derivatives such as erythrosin B and erythrosin isothiocyanate; ethidium; fluorescein and derivatives such as 5-carboxyfluorescein (FAM), 5-(4,6diсHlorotriazin-2-yDarninofluorescein (DTAF), 2'7'dimethoxy-4'5'-dichloro-6-carboxyfluorescein (JOE), fluorescein isothiocyanate (FITC), and QFITC Q(RITC); 2',7'-difluorofluorescein (OREGON GREEN®); fluorescamine; IR144; 1R1446; Malachite Green isothiocyanate; 4-methylumbelliferone; ortho cresolphthalein; nitrotyrosine; pararosaniline; Phenol Red; B-phycoerythrin; o-phthaldialdehyde; pyrene and derivatives such as pyrene, pyrene butyrate and succinimidyl 1-pyrene butyrate; Reactive Red 4 (Cibacron Brilliant Red 3B-A); rhodamine and derivatives such as 6-carboxy-X-rhodamine (ROX), 6-carboxyrhodaminс (R6G), lissamine rhodamine B sulfonyl chloride, rhodamine (Rhod), rhodamine B, rhodamine 123, rhodamine X isothiocyanate, rhodamine green, sulforhodamine B, sulforhodamine 101 and sulfonyl chloride derivative of sulforhodamine 101 (Texas Red); N,N,N',N-tetramethyl-6-carboxyrhodamine (TAMRA); tetramethyl rhodamine; tetramethyl rhodamine isothiocyanate (TRITC); riboflavin; rosolic acid and terbium chelate derivatives. Other suitable fluorophores include thiol-reactive europium chelates which emit at approximately 617 mn (Heyduk and Heyduk, Analyt. Biochem. 248:216-27, 1997; J. Biol. Chem. 274:3315-22, 1999), as well as GFP, LissamineTM, diethylaminocoumarin, fluorescein chlorotriazinyl, naphthofluorescein, 4,7-dichlororhodamine and xanthene (as described in U.S. Pat. No. 5,800,996 to Lee et al.) and derivatives thereof. Other fluorophores known to those skilled in the art can also be used, for example those available from Life Technologies (Invitrogen; Molecular Probes (Eugene, Oreg.)) and including the ALEXA FLUOR® series of dyes (for example, as described in U.S. Pat. Nos. 5,696,157, 6,130,101 and 6,716,979), the BODIPY series of dyes (dipyrromethenеboron difluoride dyes, for example as described in U.S. Pat. Nos. 4,774,339, 5,187,288, 5,248,782, 5,274,113, 5,338,854, 5,451,663 and 5,433,896), Cascade Blue (an amine reactive derivative of the sulfonated pyrene described in U.S. Pat. No. 5,132,432) and Marina Blue (U.S. Pat. No. 5,830,912).

In addition to the fluorochromes described above, a fluorescent label can be a fluorescent nanoparticle, such as a semiconductor nanocrystal, e.g., a QUANTUM DOT™ (obtained, for example, from Life Technologies (QuantumDot Corp, Invitrogen Nanocrystal Technologies, Eugene, Oreg.); see also, U.S. Pat. Nos. 6,815,064; 6,682,596; and 6,649,138). Semiconductor nanocrystals are microscopic particles having size-dependent optical and/or electrical properties. When semiconductor nanocrystals arc illuminated with a primary energy source, a secondary emission of energy occurs of a frequency that corresponds to the handgap of the semiconductor material used in the semiconductor nanocrystal. This emission can he detected as colored light of a specific wavelength or fluorescence. Semiconductor nanocrystals with different spectral characteristics arc described in e.g., U.S. Pat. No. 6,602,671. Semiconductor nanocrystals that can he coupled to a variety of biological molecules (including dNTPs and/or nucleic acids) or substrates by techniques described in, for example, Bruchez et al., Science 281 :20132016, 1998; Chan et al., Science 281:2016-2018, 1998; and U.S. Pat. No. 6,274,323. Formation of semiconductor nanocrystals of various compositions are disclosed in, e.g., U.S. Pat. Nos. 6,927,069; 6,914,256; 6,855,202; 6,709,929; 6,689,338; 6,500,622; 6,306,736; 6,225,198; 6,207,392; 6,114,038; 6,048,616; 5,990,479; 5,690,807; 5,571,018; 5,505,928; 5,262,357 and in U.S. Patent Puhlication No. 2003/0165951 as well as PCT Puhlication No. 99/26299 (puhlished May 27, 1999). Separate populations of semiconductor nanocrystals can he produced that are identifiable based on their different spectral characteristics. For example, semiconductor nanocrystals can he produced that emit light of different colors hased on their composition, size or size and composition. For example, quantum dots that emit light at different wavelengths based on size (565 mn, 655 mn, 705 mn, or 800 mn emission wavelengths), which are suitable as fluorescent labels in the probes disclosed herein are available from Life Technologies (Carlshad, Calif.).

RT-PCR is typically carried out in a thermal cycler with the capacity to illuminate each sample with a beam of light of a specified wavelength and detect the fluorescence emitted by the excited fluorophore. The thermal cycler is also able to rapidly heat and chill samples, thereby taking advantage of the physicochemical properties of the nucleic acids and thermal polymerase. The majority of the thermocyclers on the market now offer similar characteristics. Typically, thermocyclers involve a format of glass capillaries, plastics tubes, 96-well plates or 384-wells plates. The thermocylcer also involve a software analysis.

miR-92a can also be detected without amplification using the nCounter Analysis System (NanoString Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter miRNA assay kits are available from NanoString Technologies, which arc capable of distinguishing between highly similar miRNAs with great specificity. The basis of the nCounter® Analysis system is the unique code assigned to each nucleic acid target to be assayed (International Patent Application Publication No. WO 08/124847, U.S. Pat. No. 8,415,102 and Geiss et al. Nature Biotechnology. 2008. 26(3): 317-325; the contents of which arc each incorporated herein by reference in their entireties). The code is composed of an ordered series of colored fluorescent spots which create a unique barcode for each target to be assayed. A pair of probes is designed for each DNA or RNA target, a biotinylated capture probe and a reporter probe carrying the fluorescent barcode. This system is also referred to, herein, as the nanoreporter code system. Specific reporter and capture probes are synthesized for each target. The reporter probe can comprise at a least a first label attachment region to which arc attached one or more label monomers that emit light constituting a first signal; at least a second label attachment region, which is non-over-lapping with the first label attachment region, to which are attached one or more label monomers that emit light constituting a second signal; and a first target-specific sequence. Preferably, each sequence specific reporter probe comprises a target specific sequence capable of hybridizing to no more than one gene and optionally comprises at least three, or at least four label attachment regions, said attachment regions comprising one or more label monomers that emit light, constituting at least a third signal, or at least a fourth signal, respectively. The capture probe can comprise a second target-specific sequence; and a first affinity tag. In some embodiments, the capture probe can also comprise one or more label attachment regions. Preferably, the first target-specific sequence of the reporter probe and the second target-specific sequence of the capture probe hybridize to different regions of the same gene to be detected. Reporter and capture probes are all pooled into a single hybridization mixture, the "probe library". The relative abundance of each target is measured in a single multiplexed hybridization reaction. The method comprises contacting the tumor sample with a probe library, such that the presence of the target in the sample creates a probe pair—target complex. The complex is then purified. More specifically, the sample is combined with the probe library, and hybridization occurs in solution. After hybridization, the tripartite hybridized complexes (probe pairs and target) are purified in a two-step procedure using magnetic beads linked to oligonucleotides complementary to universal sequences present on the capture and reporter probes. This dual purification process allows the hybridization reaction to be driven to completion with a large excess of target-specific probes, as they are ultimately removed, and, thus, do not interfere with binding and imaging of the sample. All post hybridization steps are handled robotically on a custom liquid-handling robot (Prep Station, NanoString Technologies). Purified reactions are typically deposited by the Prep Station into individual flow cells of a sample cartridge, bound to a streptavidin-coated surface via the capture probe,electrophoresed to elongate the reporter probes, and immobilized. After processing, the sample cartridge is transferred to a fully automated imaging and data collection device (Digital Analyzer, NanoString Technologies). The expression level of a target is measured by imaging each sample and counting the number of times the code for that target is detected. For each sample, typically 600 fields-of-view (FOV) are imaged (1376×1024 pixels) representing approximately 10 mm2 of the binding surface. Typical imaging density is 100-1200 counted reporters per field of view depending on the degree of multiplexing, the amount of sample input, and overall target abundance. Data is output in simple spreadsheet format listing the number of counts per target, per sample. This system can be used along with nanoreporters. Additional disclosure regarding nanoreporters can be found in International Publication No. WO 07/076129 and WO07/076132, and US Patent Publication No. 2010/0015607 and 2010/0261026, the contents of which are incorporated herein in their entireties. Further, the term nucleic acid probes and nanoreporters can include the rationally designed (e.g. synthetic sequences) described in International Publication No. WO 2010/019826 and US Patent Publication No.2010/0047924, incorporated herein by reference in its entirety.

Mass spectroscopy can be used to quantify miRNA using RNase mapping. Isolated RNAs can be enzymatically digested with RNA endonucleases (RNases) having high specificity (e.g., RNase TI, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of posttranscriptional modifications can be revealed by mass shifts from those expected based upon the RNA sequence. Ions of anomalous mass/charge values can then be isolated for tandem MS sequencing to locate the sequence placement of the post-transcriptionally modified nucleoside. Matrix-assisted laser desorption/ionization mass spectrometry (MALDI-MS) has also been used as an analytical approach for obtaining information about posttranscriptionally modified nucleosides. MALDI-based approaches can be differentiated from ESTbased approaches by the separation step. In MALDI-MS, the mass spectrometer is used to separate the miRNA. To analyze a limited quantity of intact miRNAs, a system of capillary LC coupled with nanoES1-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nano-spray ion source, a Nanovolume Valve (Valeo Instruments), and a splitless nano HPLC system (DNa, KYA Technologies). Analyte/TEAA is loaded onto a nano-LC trap column, desalted, and then concentrated. Intact miRNAs arc eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. miR-92a can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels. miRNA can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.). Northern Blot and in situ hybridization may also be used to detect miRNAs. Suitable methods for performing Northern Blot and in situ hybridization are known in the art. Advanced sequencing methods can likewise be used as available. For example, miRNA can be detected using Illumina® Next Generation Sequencing (e.g. Sequencing-By-Synthesis or TruSeq methods, using, for example, the HiSeq, HiScan, GenomeAnalyzer, or MiSeq systems (Illumina, Inc., San Diego, Calif.)). miRNA can also be detected using Ion Torrent Sequencing (Ion Torrent Systems, Inc., Gulliford, Conn.), or other suitable methods of semiconductor sequencing.

A further aspect of the invention relates to a method of preventing or treating extracapillary glomerulonephritis, rapidly progressive glomerulonephritis (RPGN) or collapsing glomerulopathy (CG) in a subject in need thereof comprising the steps of:
 i) providing a sample from a subject,
 ii) measuring the expression level of miR-92a in the sample obtained at step i),
 iii) comparing said expression level measured in step ii) with a control, wherein high expression level of miR-92a is indicative of subject having or at risk of having or developing an extracapillary glomerulonephritis, a rapidly progressive glomerulonephritis (RPGN) or a collapsing glomerulopathy (CG), and
 iv) treating said subject having or at risk of having or developing an extracapillary glomerulonephritis, a rapidly progressive glomerulonephritis (RPGN) or a collapsing glomerulopathy (CG) with a compound according to the invention and/or an extracapillary glomerulonephritis treatment, a rapidly progressive glomerulonephritis (RPGN) treatment and/or a collapsing glomerulopathy (CG) treatment.

A further aspect of the invention relates to a method for monitoring the efficacy of a treatment for an extracapillary glomerulonephritis, a rapidly progressive glomerulonephritis (RPGN) or a collapsing glomerulopathy (CG) in a subject in need thereof.

Methods of the invention can be applied for monitoring the treatment (e.g., drug compounds) of the subject. For example, the effectiveness of an agent to affect the expression level of the miR-92a according to the invention can be monitored during treatments of subjects receiving extracapillary glomerulonephritis treatments, rapidly progressive glomerulonephritis (RPGN) treatments or collapsing glomerulopathy (CG) treatments.

The "rapidly progressive glomerulonephritis (RPGN) treatment" that is referred to in the definition of step a) above relate to any type of rapidly progressive glomerulonephritis (RPGN) therapy undergone by the rapidly progressive glomerulonephritis (RPGN) subjects previously to collecting the rapidly progressive glomerulonephritis (RPGN) tissue samples, including cyclophosphamide, plasmapheresis, anti-CD20 antibody, mycophenolate mofetil and corticosteroids such as methylpredniso lone or prednisone.

The "collapsing glomerulopathy (CG) treatment" that is referred to in the definition of step a) above relate to any type of collapsing glomerulopathy (CG) therapy undergone by the collapsing glomerulopathy (CG) subjects previously to collecting the CG tissue samples, including steroids or cyclosporine, angiotensin converting enzyme inhibitors and/or angiotensin II receptor blockers, anti-HIV therapy, lipid lowering agents and mycophenolate mofetil.

Accordingly, the present invention relates to a method for monitoring the treatment of subject affected with an extracapillary glomerulonephritis, a rapidly progressive glomerulonephritis (RPGN) or collapsing glomerulopathy (CG), said method comprising the steps consisting of:
 i) diagnosis of extracapillary glomerulonephritis, rapidly progressive glomerulonephritis (RPGN) or collapsing glomerulopathy (CU) before said treatment by performing the method of the invention
 ii) diagnosis of extracapillary glomerulonephritis, rapidly progressive glomerulonephritis (RPGN) or collapsing glomerulopathy (CG) after said treatment by performing the method of the invention
 iii) and comparing the results determined a step i) with the results determined at step ii) wherein a difference between said results is indicative of the effectiveness of the treatment.

```
Oligonucleotide sequences:
>SEQ ID NO: 1 for hsa-mir-92a-1 MI0000093
CUUUCUACACAGGUUGGGAUCGGUUGCAAUGCUGUGUUUCUGUAUGGU
AUUGCACUUGUCCCGGCCUGUUGAGUUUGG >SEQ ID NO: 2 for hsa-miR-92a-1-5p MIMAT0004507
AGGUUGGGAUCGGUUGCAAUGCU >SEQ ID NO: 3 for hsa-miR-92a-3p MIMAT0000092
UAUUGCACUUGUCCCGGCCUGU >SEQ ID NO: 4 for hsa-mir-92a-2 MI0000094
UCAUCCCUGGGUGGGGAUUUGUUGCAUUACUUGUGUUCUAUAUAAAGU
AUUGCACUUGUCCCGGCCUGUGGAAGA >SEQ ID NO: 5 for hsa-miR-92a-2-5p MIMAT0004508
GGGUGGGGAUUUGUUGCAUUAC >SEQ ID NO: 6 for hsa-miR-92a-3p MIMAT0000092
UAUUGCACUUGUCCCGGCCUGU >SEQ ID NO: 7 for anti-miR-ctrl
AAGGCAAGCUGACCCUGAAGUU >SEQ ID NO: 8 for anti-miR-92a
CAGGCCGGGACAAGUGCAAUA
```

The invention will be further illustrated by the following figures and examples. However, these examples and figures should not be interpreted in any way as limiting the scope of the present invention.

FIGURES

FIG. 1: STAT3 activation in the glomerulus during RPGN in mice and humans. Western blot analysis of phospho-STAT3 (Tyr705) and total STAT3 expression in glomeruli extracts of control and mice challenged with anti-glomerular basement membrane nephrotoxic serum (NTS). Tubulin is used as loading control. Values are means sem from at least 6 mice. ** $P<0.01$ versus control mice.

Figure 2:
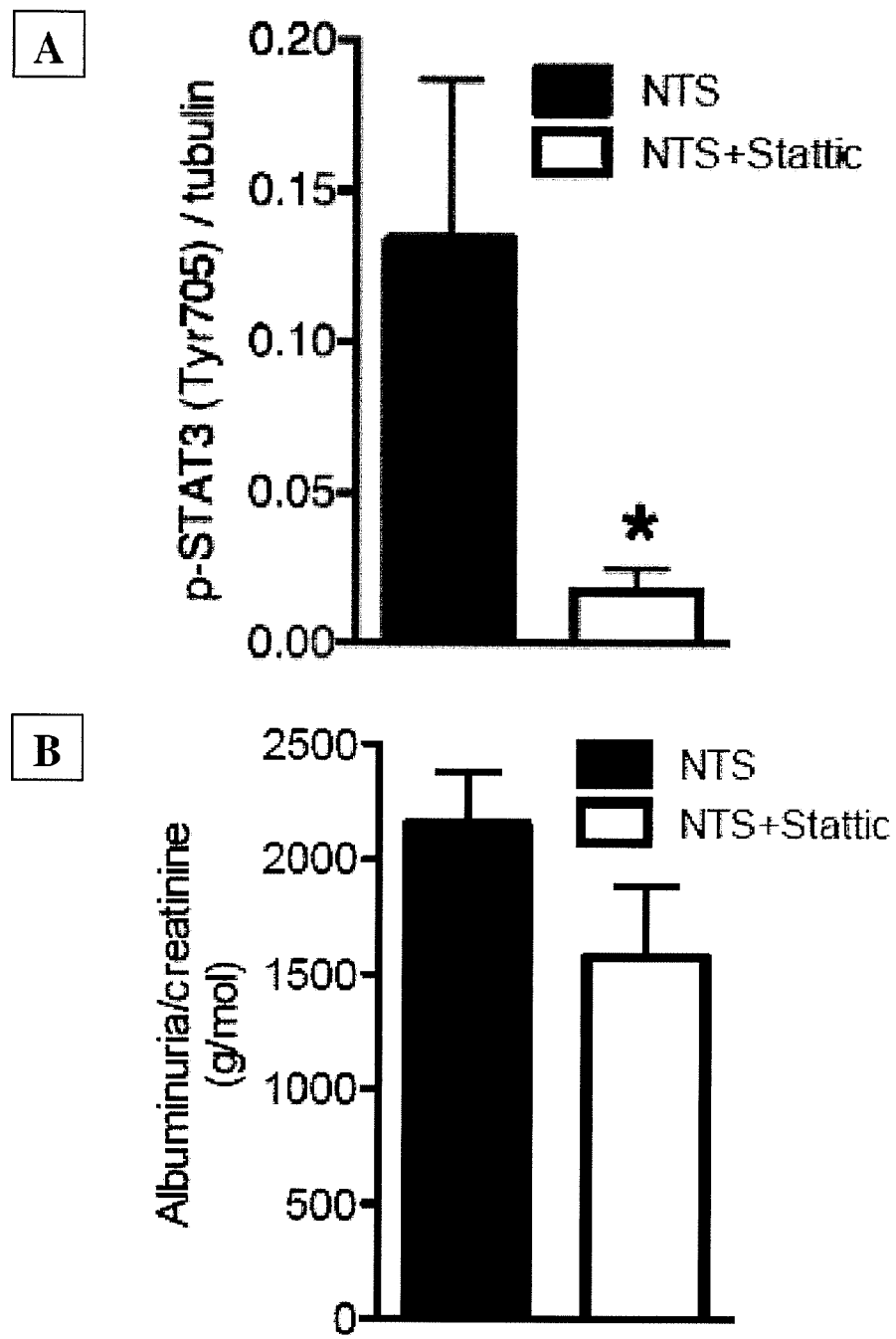
Figure 2:
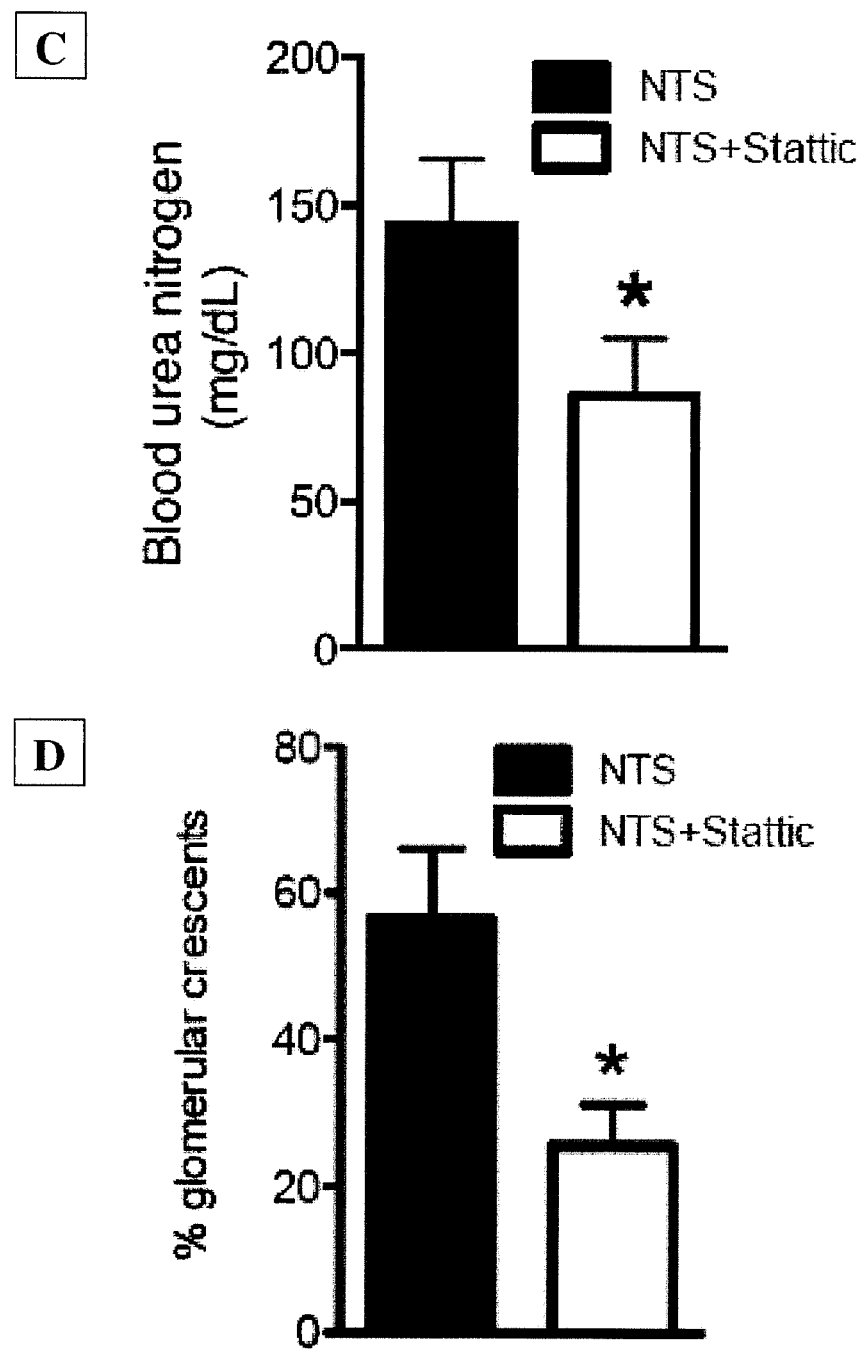

FIG. 2: STAT3 pharmacological blockade prevents renal destruction during RPGN. (A) Western blot analysis of phospho-STAT3 (Tyr705) expression in renal cortex extracts from NTS-injected mice treated with vehicle alone (NTS) and NTS-injected mice treated with Stattic, a STAT3 inhibitor, started in same time of NTS (NTS+Stattic). Tubulin is used as loading control. (B) Urinary albumin excretion rates and (C) blood urea nitrogen concentration at day 10 after NTS injection in groups of mice as in A. (D) Proportion of crescentic glomeruli in groups of mice as in A. Values arc means sem from at least 6 mice. *P $<0.05$ versus NTS-injected mice.

Figure 3:
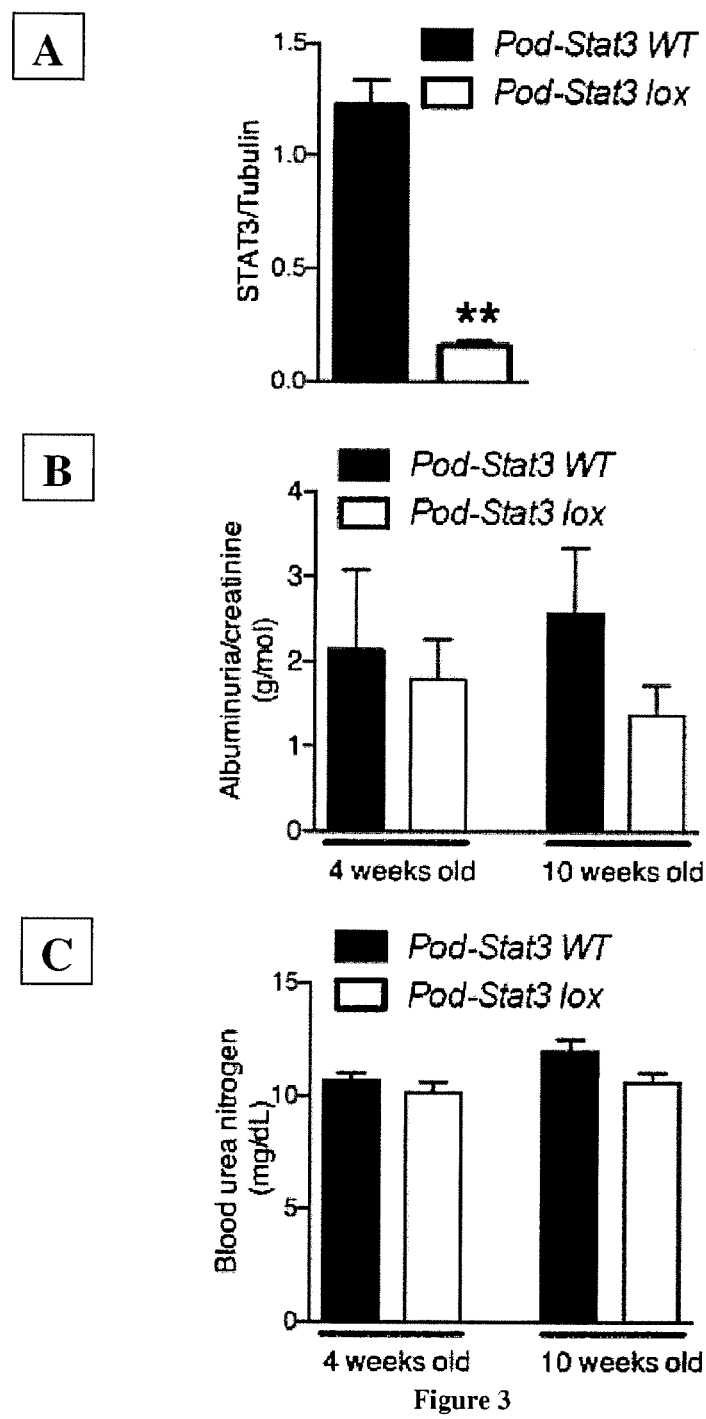

FIG. 3: Podocyte-specific deletion of Stat3 does not modify glomerular morphology and function. (A) Western blot analysis of total STAT3 expression in primary podocyte culture from Pod-Stat3 WT and Pod-Stat3 lox mice. Tubulin is used as loading control. (B) Albumin-to-creatinine ratio and (C) blood urea nitrogen concentration in Pod-Stat3 WT and Pod-Stat3 lox mice at baseline. Values are means sem (n=9 mice) ** $P<0.01$ versus Pod-Stat3 WT mice.

Figure 4:
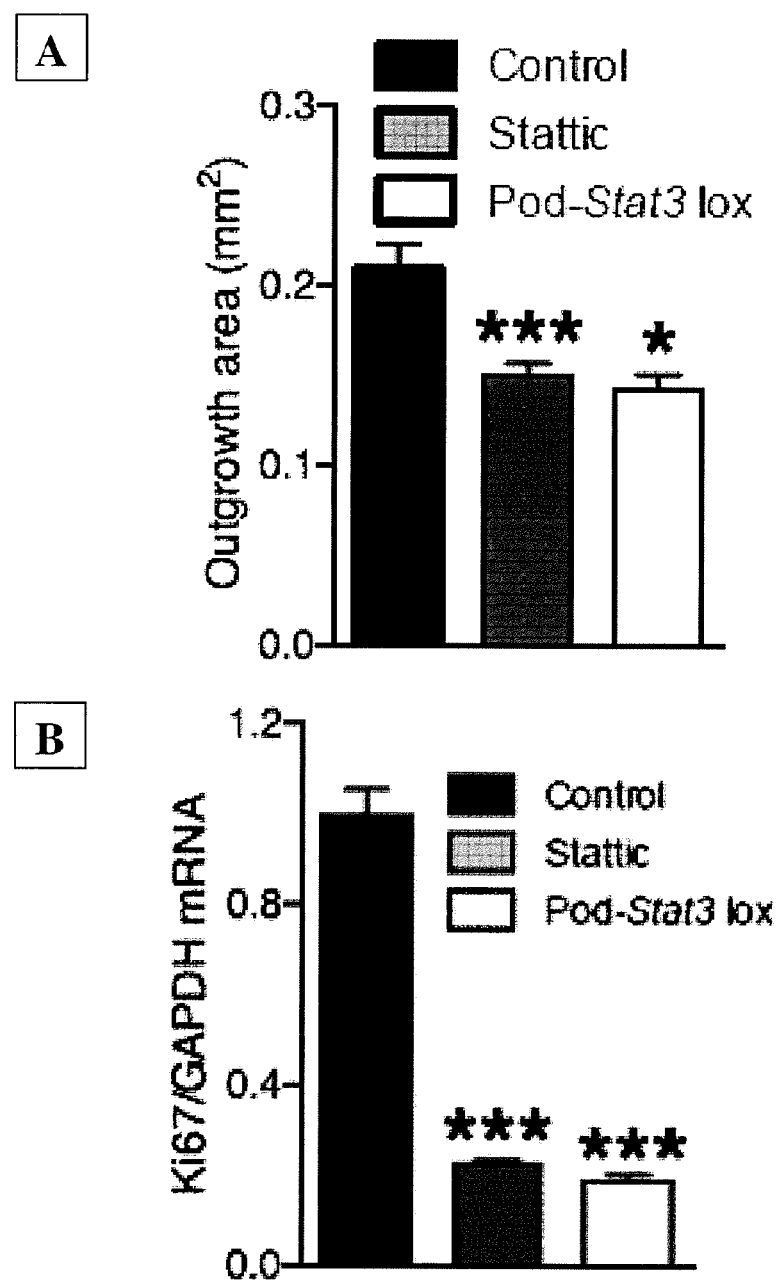
Figure 4:
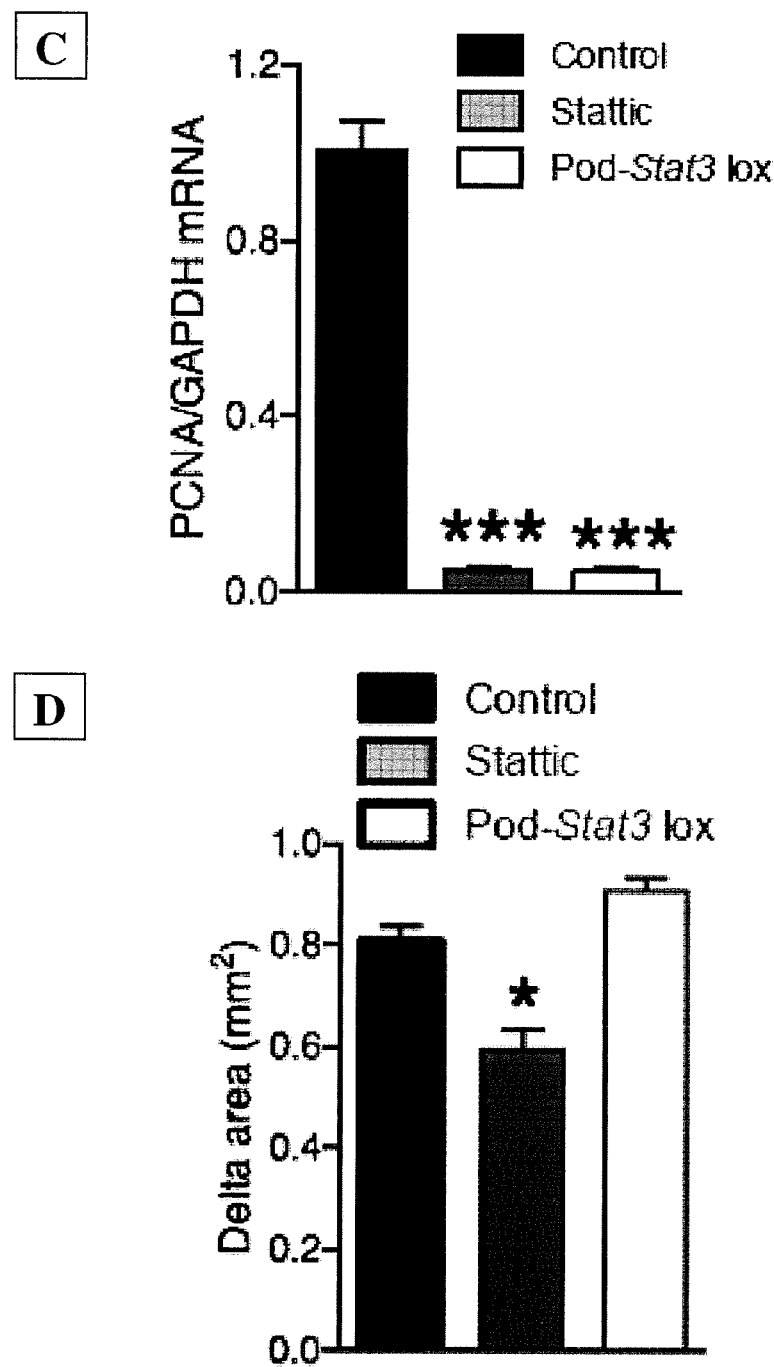

FIG. 4: Stat3 inhibition reduces proliferative and migratory podocyte phenotype in vitro. (A) Representative pictures and quantification of podocyte proliferation assay over 4 days from decapsulated glomeruli. (B and C) RT-PCR analysis of Ki67 (B) and PCNA (C) mRNA expression in primary podocyte cultures with or without Stattic (2 µM) for 16 hours or from Pod-Stat3 lox mice. (D) Representative images of wound assay showing migration within 12 hours of podocytes incubated with or without 2 µM Stattic or from Pod-Stat3 lox mice. Scale bars 100 µm. Values are means sem (n=6 mice). * $P<0.05$, *** $P<0.001$ versus untreated podocytes.

Figure 5:
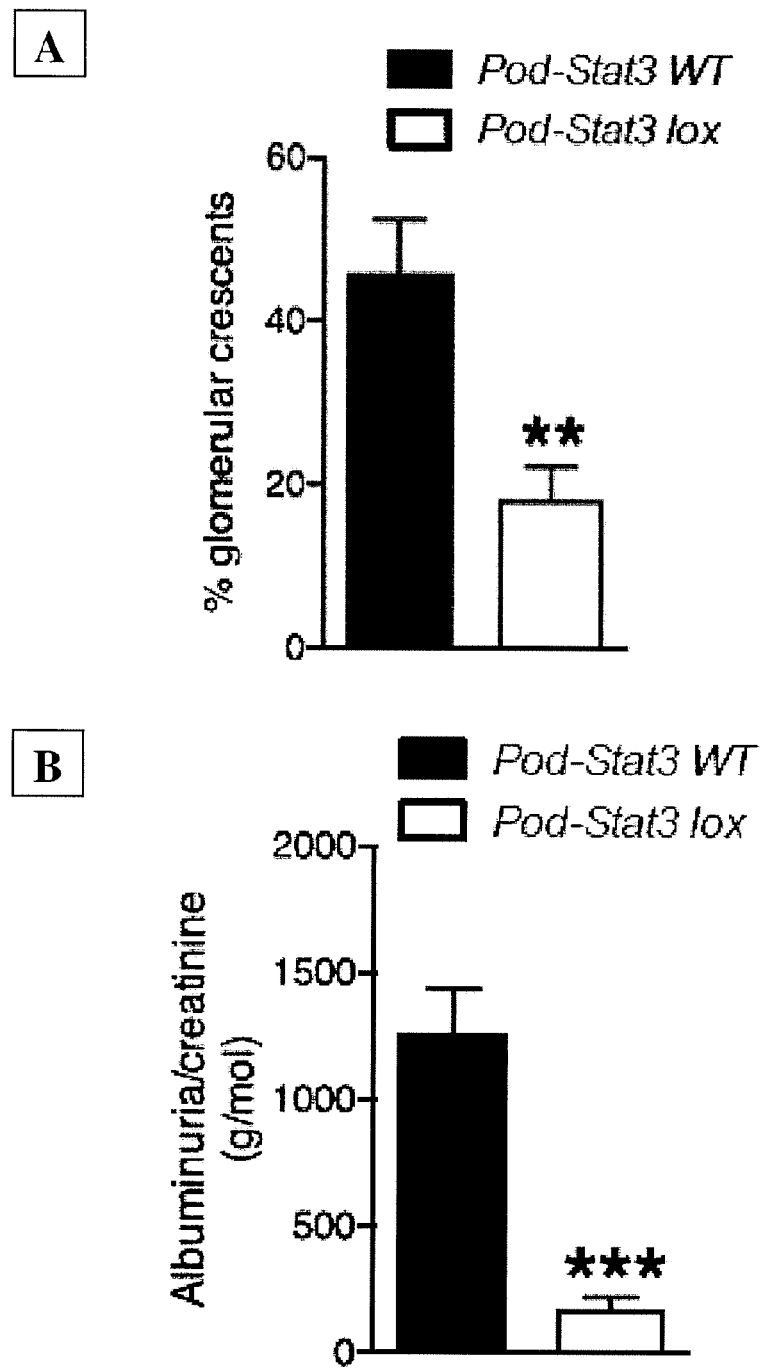
Figure 5:
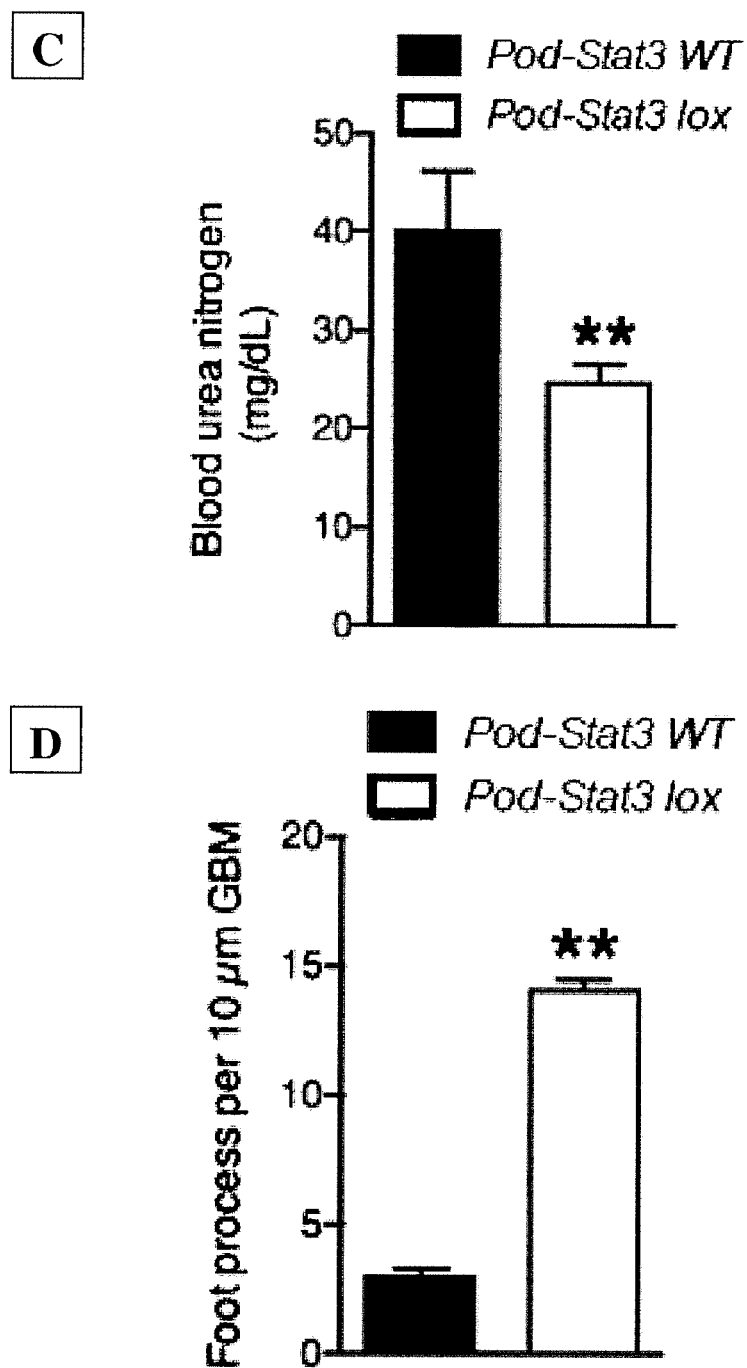

FIG. 5: Deletion, of Stat3 in podocyte protects against renal dysfunction during experimental RPGN. (A) Proportion of crescentic glomeruli in Pod-Stat3 WT and Pod-Stat3 lox mice at day 10 after NTS injection. (B and C) Albuminuria (B) and blood urea nitrogen (C) concentrations in NTS-challenged Pod-Stat3 WT and Pod-Stat3 lox mice. (D) Number of podocyte foot processes per 10 µm glomerular basement membrane (GBM) length. Values are means sem from at least 5 mice.  $P<0.01$ ; * $P<0.001$ versus NTS-challenged Pod-Stat3 WT mice.

Figure 6:
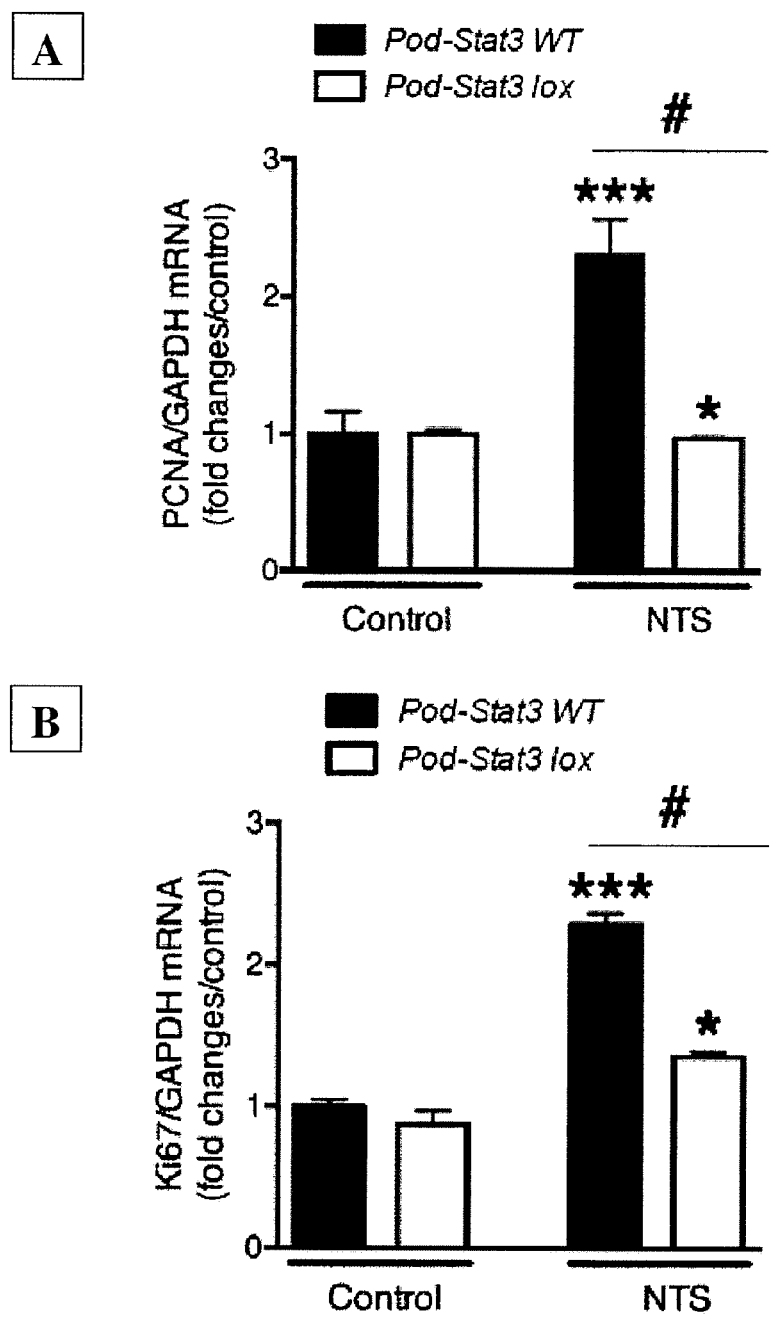

FIG. 6: Podocyte-specific deletion of Stat3 decreases glomerular epithelial cells proliferation in RPGN. (A and B) RT-PCR analysis of Ki67 (A) and PCNA (B) mRNA expression in isolated glomeruli from unchallenged or NTS-injected Pod-Stat3 WT and Pod-Stat3 lox mice. Values are means sem from at least 6 mice.  $P<0.01$ ; * $P<0.001$ versus non challenged mice and # $P<0.001$ versus NTS-challenged Pod-Stat3 WT mice.

Figure 7:
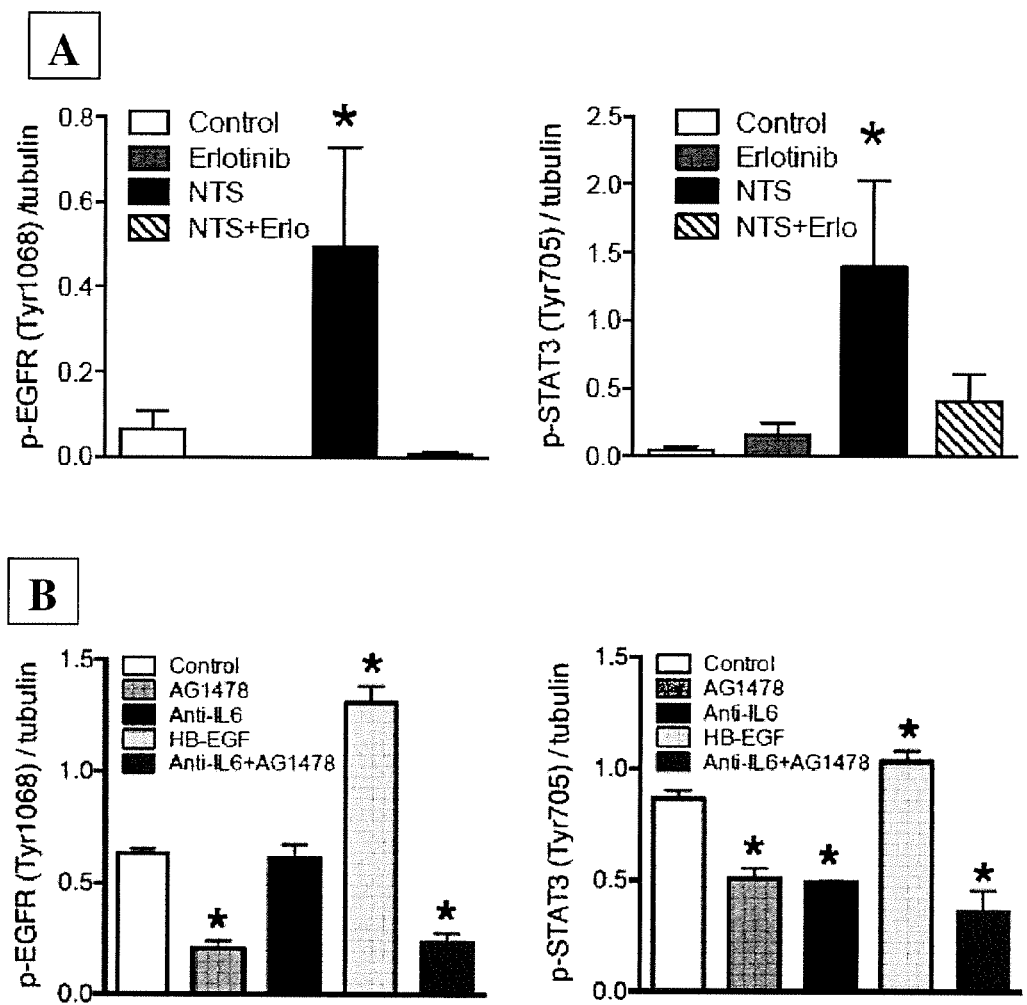

FIG. 7: Upstream pathways of Stat3 activation in podocytes. (A) Western blot analysis and quantification of phospho-EGFR (Tyr1068) and phospho-Stat3 (Tyr705) expression in kidney cortex from control or NTS-challenged mice with or without erlotinib (10 mg/kg/day), a specific inhibitor of EGFR. Tubulin is used as loading control. Values are means sem from at least 5 mice per condition. * $P<0.05$ versus unchallenged mice (control). (B) Western blot analysis and quantification of phospho-EGFR (Tyr1068) and phospho-STAT3 (Tyr705) on primary culture of podocytes after addition of AG1478 (EGFR kinase inhibitor), anti-mIL-6 monoclonal antibody or HB-EGF for 16 hours. Values are means sem from at least 5 western blot. * $P<0.05$ versus untreated podocytes (control).

Figure 8:
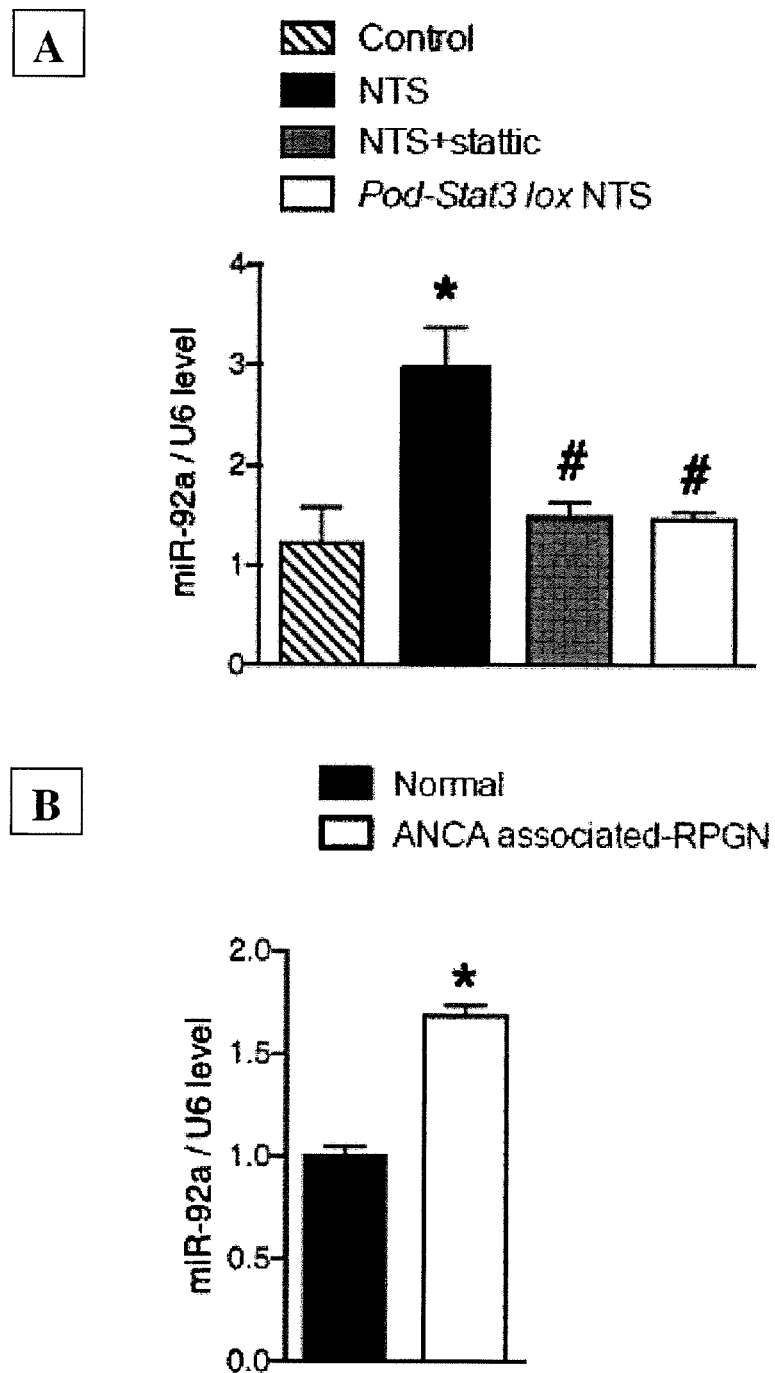

FIG. 8: Upregulation of miR-92a expression with RPGN in mouse and human kidneys. (A) RT-qPCR for miR-92a normalized to U6 and relative to control in the renal cortex from normal mouse kidneys or NTS-challenged mice or NTS-challenged mice with Stattic or NTS-challenged s mice. Values arc means sem (n=4 per group). * $P<0.05$ vs. control, † $P<0.05$ vs. NTS alone. (B) Relative expression of hsa-mir-92a in kidney biopsies from individuals diagnosed with ANCA-associated vasculitis and RPGN and normal kidney samples. Values are means sem (n=4 per group). * $P<0.05$ vs. normal.

Figure 9:
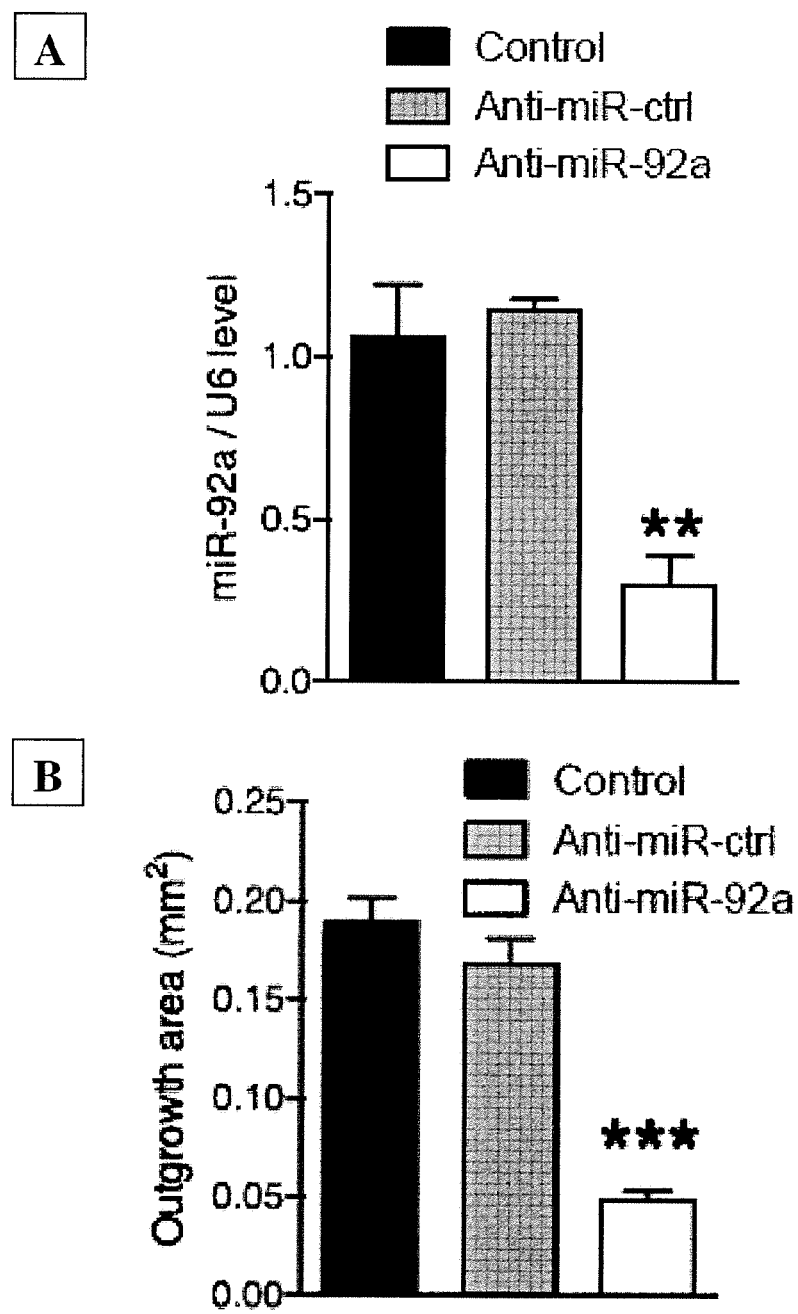
Figure 9:
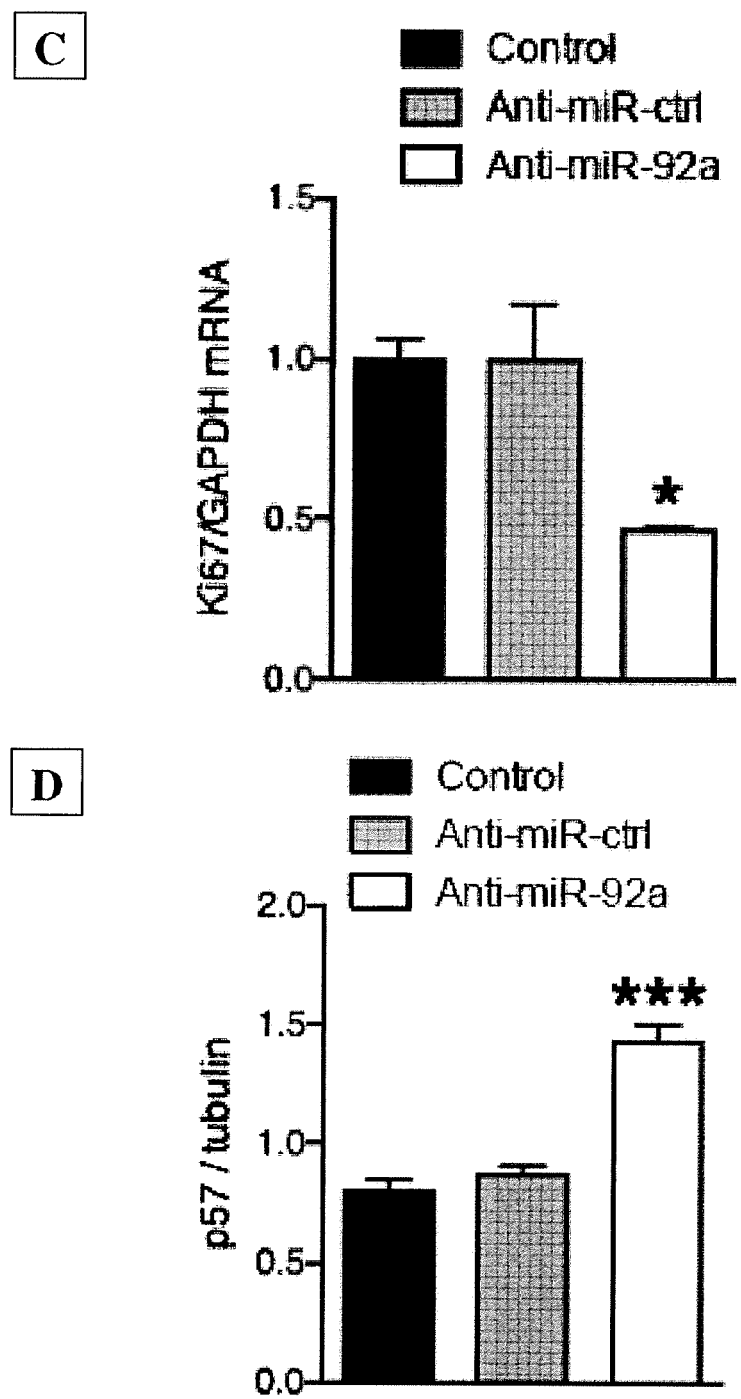

FIG. 9: Inhibition of miR-92a in cultured podocytes decrease proliferation with p57 upregulation. (A) RT-qPCR for miR-92a normalized to U6 and relative to control in podocytes transfected with an anti-miR-control (anti-miR-ctrl) or an anti-miR-92a. (B) Representative pictures and quantification of podocyte proliferation assay over 4 days from decapsulated mouse glomeruli. (C) RT-PCR analysis of Ki67 mRNA expression in primary podocyte cultures with or without inhibition of miR-92a. (D) Western blot analysis and quantification of p57 protein expression in primary cultured podocytes with or without inhibition of miR-92a. Tubulin is used as loading control. Values are means sem (n=4 per group). * $P<0.05$, $P<0.01$ and *** $P<0.001$ versus control podocytes (control).

Figure 10:
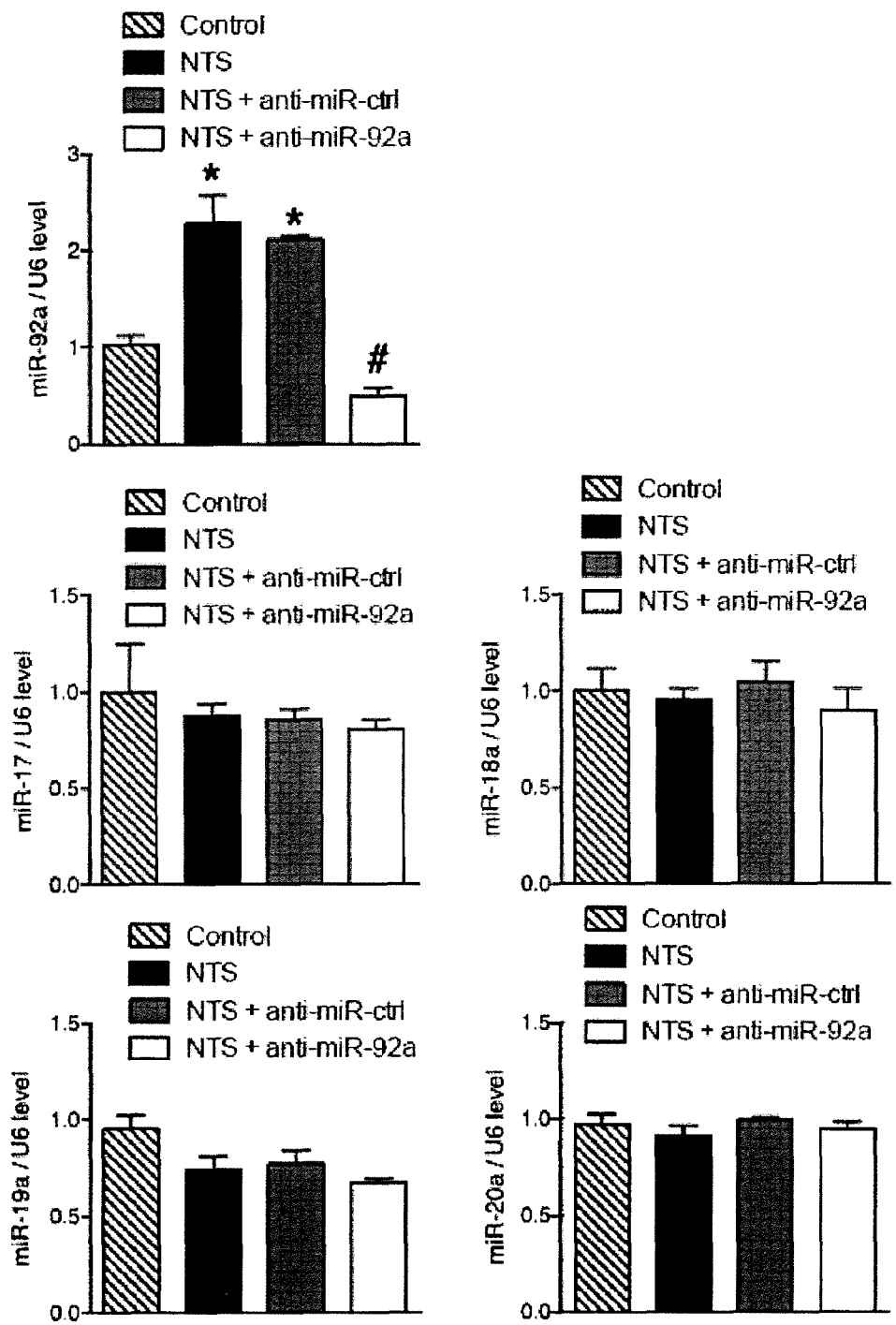

FIG. 10: Only the miR-92a member of the the miR-17-92 microRNA cluster is upregulated in injured glomeruli. RT-qPCR expression analysis for miR-92a, miR-17. miR-18a, miR-19a and miR-20a normalized to U6 and relative to control in freshly isolated glomeruli from normal mice (control), NTS-challenged mice (NTS), NTS-challenged mice treated with anti-miR-control (anti-miR-ctrl) and NTS-challenged mice treated with anti-miR-92a (anti-miR-92a) after 10 days.

Figure 11:
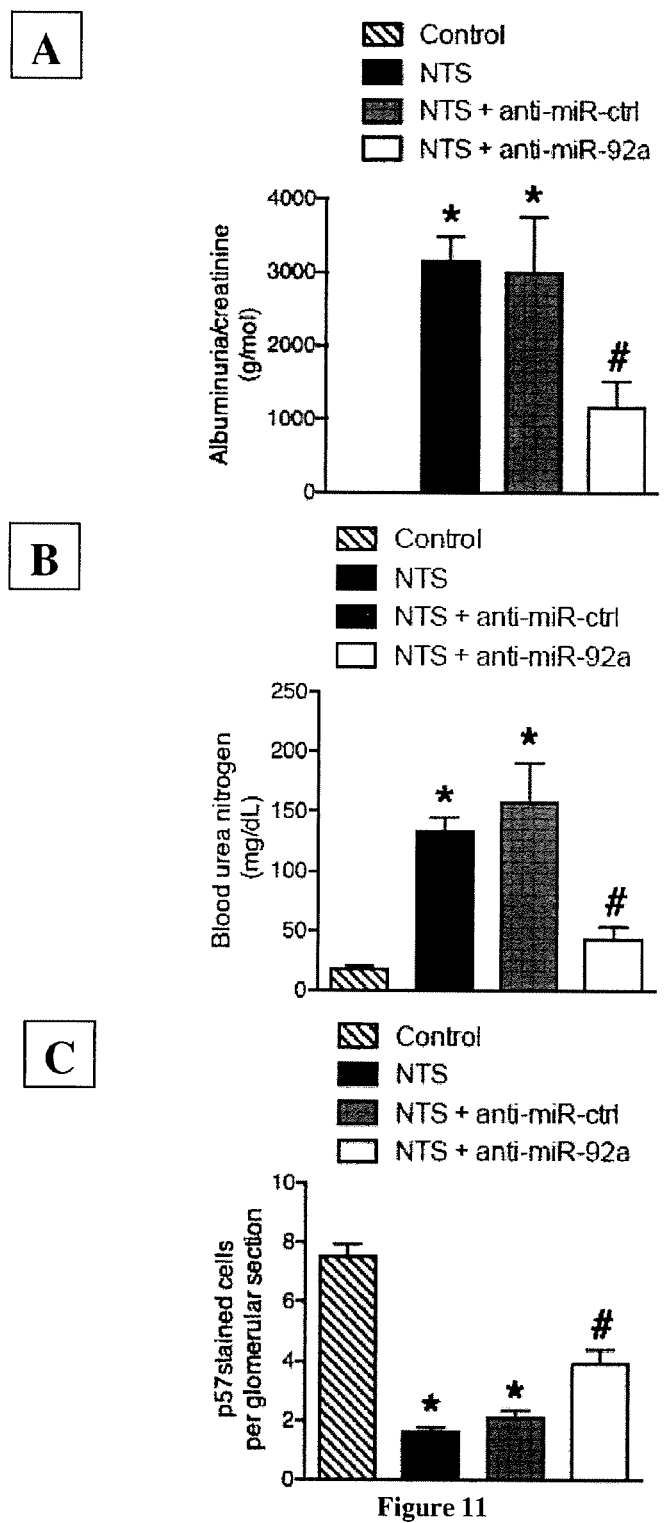

FIG. 11: Silencing miR-92a decreases kidney injury in mouse model of RPGN. (A) and blood urea nitrogen concentrations (B) in normal mice (control), NTS-challenged mice (NTS), NTS-challenged mice treated with anti-miR-control (anti-miR-ctrl) and NTS-challenged mice treated with anti-miR-92a (anti-miR-92a) 10 days after NTS injection. Values are means sem (n=4 per group). * $P<0.05$ versus control, # $P<0.05$ vs. NTS alone.

Figure 12:
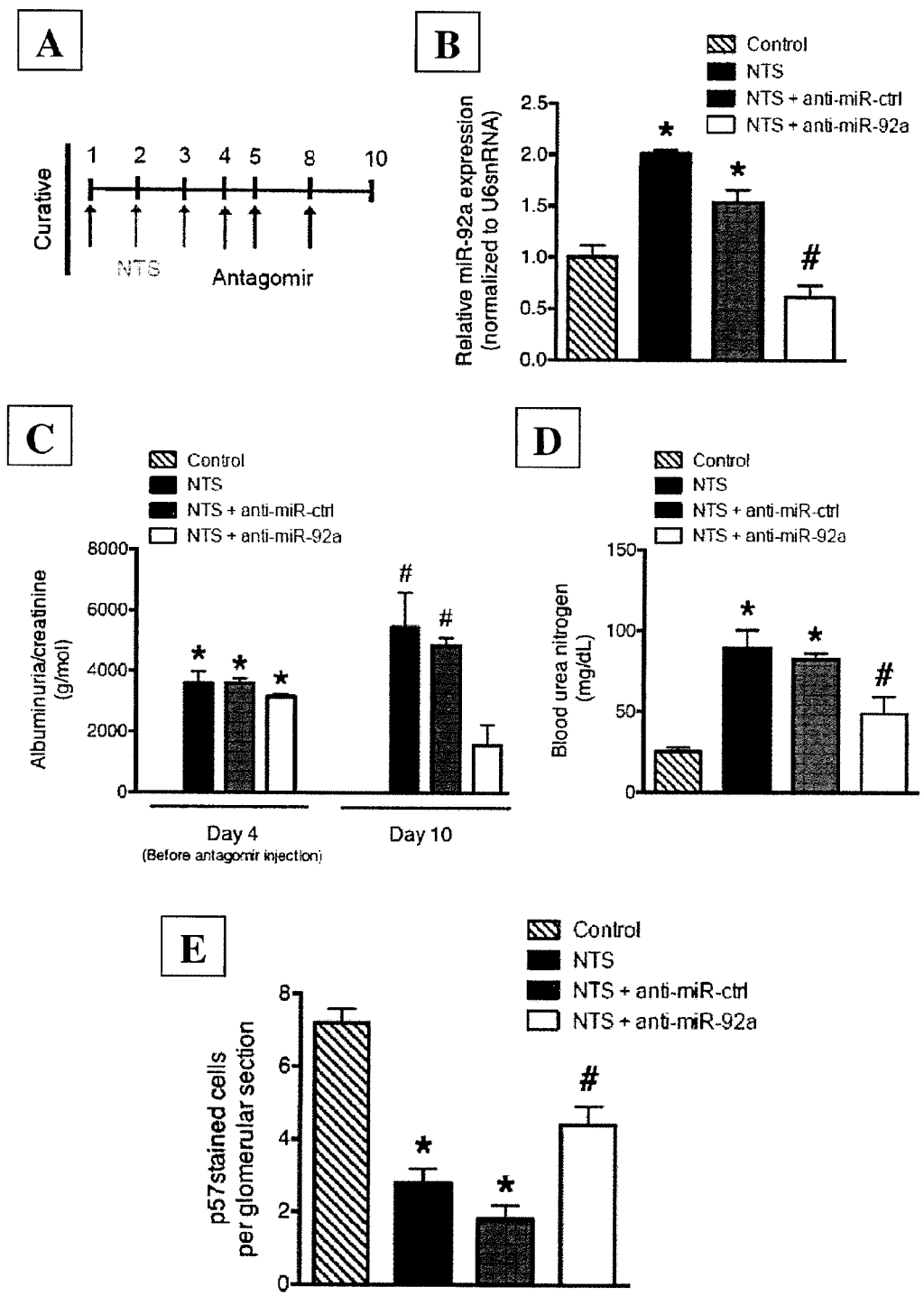

FIG. 12: miR-92a in vivo silencing prevents and abolishes RPGN development. (A) Study design of the in vivo antagomir experiment. (B) Relative miR-92a expression in dynebeads isolated glomeruli from normal mice (control), NTS-challenged mice (NTS), NTS-challenged mice treated with anti-miR-control (anti-miR-ctrl) and NTS-challenged mice treated with anti-miR-92a (anti-miR-92a) after 10 days. All values are normalized to U6 and arc relative to control. Values arc means±sem (n=5 per group). * $p<0.05$ vs. control, # $p<0.05$ vs. NTS alone. (C) Urinary albumin excretion rates at day 4 (before antagomir injection) and at day 10 after NTS injection. Scale bars 10 µm. (D) Blood urea nitrogen concentration at day 10 after NTS injection in control or NTS-challenged mice. Values are means±sem (n=10 mice per group). (E) Quantification of p57-positive cells per glomerular section in mice described in (a). Values are means±sem (n=10 per group). * $p<0.05$, # $p<0.05$ vs. NTS alone (NTS).

EXAMPLES

Example 1

Material & Methods

Animals

Podocyte-specific disruption of Stat3 mice were generated by crossing podocin-Cre positive mice (63) with Stat3 floxed mice (64) on C57BL6/J background. Their age-matched littermates with no deletion of Stat3 in any cells are considered as controls. Pharmacological inhibition of Stat3 was achieved with Stattic, a non-peptidic small molecule that selectively inhibits activation, dimerization and nuclear translocation of STAT3 (65). Stattic (25 mg/kg) was administered in i.p. way every other day for 10 days. 10 weeks old 129S2/SvPasCr male mice were randomly treated with Stattic and were compared to vehicle-treated (DMSO) littermates.

Experiments were conducted according to the French veterinary guidelines and those formulated by the European Community for experimental animal use (L358-86/609EEC), and were approved by the Institut National de la Santéet de la Recherche Médicate and local University Research Ethics Committee (file 12-62, Comitéd'Ethique en matière d'Expérimentation Animate, Paris Descartes).

Human Tissues

Formalin-fixed, paraffin-embedded renal tissue specimens obtained at the Hôpital Européen Georges Pompidou, Assistance Publique-Hôpitaux de Paris, Paris, France, were included in this study. Human tissue was used after approval by, and following the guidelines of, the local Ethics Committee. Renal biopsy cases with sufficient tissue for immunohistochemical evaluation after completion of diagnostic workup were included. Normal adult human kidney tissue was obtained from kidneys surgically excised because of the presence of a localized neoplasm.

Induction of Crescentic Glomerulonephritis

The glomerulonephritis was induced on male mice (10-12 weeks of age) by intravenous injection of 15 µL of sheep anti-glomerular basement membrane (GBM) nephrotoxic serum (NTS), which was diluted with 85 µL of sterile phosphate buffer solution. Serum injections were repeated twice (on days 2 and 3) at 6 µL/g of body weight and 7 µL/g respectively.

Biochemical Measurements in Blood and Urine

Urinary creatinine and blood urea nitrogen (BUN) concentrations were analyzed by a standard colorimetric method (Olympus AU400) at the Biochemistry Laboratory of Institut Claude Bernard (IFR2, Faculté de Médecine Paris Diderot). Urinary albumin excretion was measured using a specific ELISA assay for quantitative determination of albumin in mouse urine (CellTrend GmbH).

Glomeruli Isolation and in Vitro Assays in Cultured Podocytes

Mouse kidneys were extracted, minced, and digested in 2 mg/mL collagenase I solution (Gibco) in RPMI 1640 (Invitrogen) at 37° C. for 3 minutes, then filtered through a 70-µm cell strainer and one more through a 40-µm cell strainer. The homogenate was centrifuged at 720 g for 6 minutes and cells plated. Isolated glomeruli were then collected in Phosphosafc extraction buffer (Novagen) for protein extraction or in RLT extraction buffer (Qiagen) for total RNA extraction. For podocyte primary culture, freshly isolated glomeruli were plated in 6-plate dishes in RPMI 1640 (Invitrogen) supplemented by 10% Fetal Calf Serum (Biowest) and 1% penicillin-streptomycin (Invitrogen). The outgrowth of podocytes started between days 2 and 3. Podocyte outgrowth area was quantified at day 4 using ImageJ software.

After 4 days of primary culture, podocytes were trypsinized then plated into µ-Dish 35 mm high with Culture-Insert (Ibidi). Ibidi's wounding inserts were used for cell migration studies. The coverage of the 500-µm gap was assessed after 12 hours of culture and podocyte migration area was quantified using ImageJ software. The effects of HB-EGF (10 ng/mL, Preprotech) or AG1478 (1 µM, Calbiochem) or anti-mIL-6 monoclonal antibody MP5-20F3 (10 µg/mL, eBiosciences) or Stattic (2 µM, Calbiochem) on differentiated podocytes was applied during 16 hours. After stimulation, podocytes were scrapped in Phosphosafe buffer for protein extraction or in RLT buffer for total RNA extraction.

Histology

Kidneys were harvested and fixed in 4% formal. Paraffin-embedded sections (5 µm thick) were stained by Masson's trichrome to evaluate kidney morphology and determine proportion of crescentic glomeruli by a blinded examination on at least 50 glomeruli per section.

Immunohistochemistry and Immunofluorescence

Deparaffinized kidney sections were incubated for 30 minutes at 95° C. in the target retrieval solution (S1699, Dako), then in peroxidase blocking reagent (S2001, Dako), blocked in PBS containing 5% BSA and immunostained against phospho-STAT3 (Tyr705) (Cell Signaling Technology) and phospho-STAT3 (Tyr705) (Millipore), STAT3 (Cell Signaling Technology), podocalyxin (R&D systems), Ki-67 (Abeam) and p57 (Santa Cruz Technology). For phospho-STAT3, Ki-67 and p57, specific staining was revealed using Histofine reagents (Nichirei Biosciences), which contained anti-rabbit (414341F) or anti-goat (414161F) immune-peroxidase polymer for mouse tissue sections. For STAT3 and podocalyxin immunofluorescence, primary antibody incubation was followed by a secondary rabbit anti-goat IgG AF488-conjugated antibody (Invitrogen, 1:400) and a secondary rabbit anti-goat IgG AF594-conjugated antibody (Invitrogen, 1:400) respectively. Podocyte culture cells were immunostained against podocin (ab50339 Abeam), nephrin (ab58968 Abeam), WTI (ab15249 Abeam) or p57 (Santa Cruz Biotechnology). The nuclei were stained using DAPI. Images were obtained with an Axioimager Z1 apotome (Zeiss).

Transmission Electron Microscopy Procedure

Small pieces of renal cortex were fixed in 4% glutaraldehyde, postfixcd in 1% osmium tetroxide and embedded in epoxy resin. Ultrathin sections were counterstained with uranyl acetate and examined in a JEOL 1011 transmission electron microscope with Digital Micrograph software for acquisition. Measurements of podocyte foot process, per 10 µm of glomerular basement membrane (GBM), were made on the resulting photographs by counting manually. Results for 100 µm of GBM were averaged.

Western Blot Analysis

After extraction from glomeruli or podocytes with lysis buffer, proteins were quantified by BCA protein assay kit (iNtRON Biotechnology). Samples were resolved on 4-12% Bis-Tris Criterion XT gels (Bio-Rad) then transferred to a polyvinylidene difloride membrane. Membranes were incubated with the appropriate primary antibodies: rabbit anti-phospho-EGFR (Tyr1068) (Cell Signaling Technology), rabbit anti-phospho-STAT3 (Tyr705) (Cell Signaling Technology), goat anti-p57 (Santa Cruz Biotechnology). Protein loading was monitored by using the rat anti-tubulin antibody (Abeam). Secondary antibodies were donkey-anti rabbit HRP and donkey-anti rabbit HRP (GE Healthcare Life Sciences). Antigens were revealed by enhanced chemiluminescence (Supersignal West Pico, Pierce) and detected on a LAS-4000 imaging system (Fuji). Densitometric analysis with ImageJ software was used for quantification.

Real-Time PCR

Total RNA extraction of mice glomeruli was performed using an Rneasy Minikit (Qiagen) and reverse transcribed into cDNA using the Quantitect Reverse Transcription kit (Qiagen) according to the manufacturer's protocol. cDNA and standard were amplified in Maxima SYBR Green/Rox qPCR mix (Fermentas) on an ABI PRISM thermo cycler. The comparative method of relative quantification (2-ΔΔCT) was used to calculate the expression level of each target gene, normalized to GAPDH. The oligonucleotide sequences are available upon request. The data are presented as the fold change in gene expression.

For miRNA expression analysis, RNA from kidney cortex were prepared with Trizol (Life Technologies) according to manufacturer's instructions. miRNA expression was determined using Taqman miRNA assay (Life technologies) according to manufacturer's protocols. U6 snRNA was used as endogenous control.

miR-92a in Situ Hybridization

In situ hybridization was performed as previously described by Bonaucr et al (66). Briefly, 5 μm-thick kidney paraffin embedded sections were cut and fixed in PFA 4% for 10 min. Then sections were washed with 1× PBS and then acetylated for 10 min. After washes, sections were incubated with protein kinase K (Sigma-Aldrich) for 10 min. at 37° C. After washings, sections were incubated with hybridization buffer for 5 h at room temperature. miRNA probes (miR-92a probe double-DIG labeled LNA probes, Exiqon, final concentration 20 nM) was mixed with denaturation buffer and added to the sections followed by incubation over night at 56° C. U6snRNA probe (3'-DIG labeled LAN, probe, Exiqon) was used at 10 nM final concentration and as a positive control. The day after, sections were washed in successive decreasing SSC buffers for 5 min at 56° C. (5×1 time, 1×2 times, 0.2×3 times) and then washed. After incubation for 1 hour in blocking solution (B1 solution +3% fetal calf serum +0.1% Tween-20), sections were incubated with anti-DIG AP antibody (Roche; 1:2000) overnight at 4° C. After washings, sections were incubated with NBT/BCIP (Promega) in NTMT+levamisole (0,2 mM/L) for 48 hours in the dark at RT. NBT/BCIP was changed every 12 hrs. Afterwards, slides were fixed in PFA 4% for 30 min and mounted with Fluoprep mounting medium (Biomerieux).

In Vivo MiR-92a Inhibition in Wild-Type Mice

For preventive strategy, antagomiR treatment (12 mg/kg) started 3 days before NTS injection. AntagomiRs (VBC biotech, Vienna) were delivered by retro-orbital i.v. injections under brief anesthesia. Second and third injections were performed on days 1 and 3 with NTS injection. For curative strategy, antagomir were injected on days 4, 5 and 8 after NTS. A scramble antagomiR (Antagomir-Control) was used as control. The sequences were obtained from previously published manuscript (66). In the miR-92 antagomir and control antagomir, the 2'O RNA base are methylated followed by first two bases and last 3 bases are phosphorothiated to increase the stability of antagomir from degradation. In addition, a cholesterol-TEG was added at the 3' for easy entry of antagomir into the cells. AntagomiR-Control (SEQ ID NO: 7, anti-miR-ctrl): 5'-AAGGCAAGCUGAC-CCUGAAGUU-3' and antagomiR-92a (SEQ ID NO: 8, anti-miR-92a): 5'-CAGGCCGGGACAAGUGCAAUA-3' as shown to be effective after in vivo administration in kidneys (34, 67). Saline-treated mice were used as control of the scramble antagomiR.

miR-92a in Vitro Modulation

MicroRNA-92a inhibition was achieved in vitro by transfecting primary culture podocytes with anti-miR-92a inhibitor using Hiperfect transfection reagent (Qiagen). Anti-miR-Control#1 was used as control (All from Ambion, 50 nM).

Statistical Analyses

All values are expressed as means+SEM. Statistical analyses were calculated using GraphPad Prism software (La Jolla, Calif.). Comparison between two groups was performed by using Mann-Whitney t test. Comparison between multiple groups was performed by using one-way ANOVA followed by Tukey post test. Values of $P<0.05$ were considered significant.

Results

Activation of STAT3 in Glomeruli During Crescentic RPGN in Mice and Humans

Recently, the inventors found that EGFR activation in podocytes is involved in glomerular injury and renal failure during RPGN (8). To decipher the signaling pathway implicated in RPGN, the inventors investigated downstream signals in the EGFR pathway. STAT3 activation was studied in kidney harvested 10 days after injection of anti-GBM nephrotoxic serum (NTS) into mice. First, phosphorylation of STAT3 on tyrosine 705 appeared in freshly isolated glomeruli from NTS-treated than control animals (FIG. 1). To determine which cell type evinced an activation of STAT3, the inventors performed immunohistochemistry on kidney biopsies from NTS-challenged and control mice. In non-treated mice, STAT3 is exclusively phosphorylated in tubular cells. A staining for phospho-STAT3 (Tyr705) appeared in glomerular cells as podocytes of NTS-treated mice. To evaluate the relevance of this finding to human disease, the inventors performed immunohistochemical staining of kidney sections from 6 patients diagnosed with RPGN complicating Anti-Neutrophil Cytoplasmic Autoantibody (ANCA) vasculitis. All sections of kidney biopsies showed a staining for phospho-STAT3 in podocytes and in crescents.

STAT3 Pharmacological Blockade Prevents Renal Destruction During RPGN

To determine whether blockade of STAT3 activation could represent a possible therapeutic complement for treatment of RPGN as found with FFGR kinase inhibitors (8), the inventors injected concomitantly NTS and Stattic, a STAT3 inhibitor (8) to WT mice with the 129S2 genetic background that is markedly prone to crescent formation and glomerular damage upon NTS administration. Stattic administration significantly reduced STAT3 (Tyr705) phosphorylation in glomeruli after 10 days of severe experimental RPGN (FIG. 2A). STAT3 inhibition induced a trend to decreased albuminuria (FIG. 2B), significantly alleviated the rise in blood urea nitrogen (BUN) concentrations by 50% (FIG. 2C) and reduced the proportion of crescentic glomeruli (FIG. 2D). Overall, administration of systemic STAT3 inhibitor had marked effects on renal damage, inflammation and renal failure in this severe experimental model of RPGN.

Deletion of Stat3 Prevents Switch in Podocyte Phenotype

To abolish STAT3 expression specifically in podocyte, the inventors bred mice in order to obtain mice with Stat3 floxed and podocyte-specific Cre expression (Pod). To verify STAT3 deficiency in podocytes, the inventors performed immunofluorescence detection of total STAT3 protein and podocalyxin, as cell surface marker of podocyte, in kidney sections of Pod-Stat3 lox and Pod-Stat3 WT mice. Double staining of sections revealed marked constitutive expression of STAT3 in podocytes of glomeruli from Pod-Stat3 WT mice. The inventors show that STAT3 staining is nearly absent in podocytes from Pod-Stat3 lox mice. Deletion of STAT3 was also confirmed in primary culture of podocyte from Pod-Stat3 lox and Pod-Stat3 WT mice. Western blot analysis showed a significant decrease in STAT3 expression in cultured primary podocytes (change, −88%) (FIG. 3A). It should be noticed that after isolation from kidney, less than 5% of cells were other glomerular cells than podocytes (WTI/podocin negative cells).

Pocl-Stat3 lox mice showed no abnormalities in glomerular morphology, urinary albumin excretion and renal function estimated by BUN (FIG. 3B and C). Thus, Stat3 alleles deletion in podocytes did not disturb renal phenotype at baseline. the inventors next isolated glomeruli from Pod-Stat3 lox and Pod-Stat3 WT mice to compare podocyte proliferation and migration, hallmarks of podocyte dedifferentiation and crescent formation. Thus, as an in vitro assay for podocyte crescent formation, the inventors measured outgrowth of podocytes from isolated decapsulated mouse glomeruli. When cultured for 7 days, 95% of cells still exhibit podocin, nephrin and WTI expression. Podocyte outgrowth area was significantly reduced around glomeruli isolated from Pod-Stat3 lox mice or in Pod-Stat3 WT podocytes treated with STAT3 inhibitor (FIG. 4A). Likewise, genetic or pharmacological alteration of STAT3 markedly blunted Ki67 and PCNA expression in primary podocytes (FIG. 4B and C). By contrast, STAT3 inhibition or podocyte-specific deletion of Stat3 displayed little or no effect on the migratory phenotype (FIG. 4D).

Podocyte-Specific Deletion of Stat3 Protects Against Renal Destruction During RPGN To study in vivo the relative contribution of STAT3 in podocytes in the development of inflammatory glomerular injury, the inventors challenged Pod-Stat3 lox mice with NTS. As expected, Pod-Stat3 WT mice exhibited crescent formation, and renal dysfunction. However, Pod-Stat3 lox mice displayed a marked 60% decrease in crescent formation evaluated in Masson's trichrome stained sections (FIG. 5A). Furthermore, this histological observation was associated with preserved renal function in Pod-Stat3 lox animals only, as shown by reduced urinary albumin to creatinine ratio (FIG. 5B) and normal BUN (FIG. 5C) concentrations. Podocyte-specific deletion of Stat3 also attenuated ultrastructural alterations of podocytes and full loss of interdigitating foot process pattern. The counted foot process per 10 µm of GBM is 5-fold higher in Pod-Stat3 lox mice, suggesting a conservation of podocyte ultrastructure and differentiated cytoskeletal architecture (FIG. 5D). To decipher the role of STAT3 on podocyte phenotype in vivo, the inventors performed real-time PCR for Ki67 and PCNA mRNA expression in freshly isolated glomeruli from unchallenged and NTS-challenged Pod-Stat3 lox and Pod-Stat3 WT mice. Administration of NTS upregulated PCNA (change, +130%) (FIG. 6A) and Ki67 (change, +128%) (FIG. 6B) mRNA levels in freshly isolated glomeruli from Pod-Stat3 WT mice. NTS-induced Ki67 glomerular expression was found in podocytes and parietal epithelial cells (PECs) only. This effect of NTS on ki67 and PCNA mRNA levels was almost completely abolished by Stat3 deletion in podocyte (FIGS. 6A, and B). Taken together these findings suggest that Pod-Stat3 lox mice were protected from NTS-induced crescent formation and loss of renal function.

Upstream Inducers of STAT3 Activation in Podocytes.

Known stimulators of STAT3 signaling are ligand-mediated activation of gp130 receptor and epidermal growth factor (EGF) receptor (18-20) by IL-6 (21-23), IL-10 (24-26) and EGFR ligands such as HB-EGF (27), respectively. The inventors first focused on the HB-EGF/EGFR pathway because activation of this pathway in podocytes was found to aggravate RPGN (8). Assessment of p-EGFR and p-STAT3 expression in freshly isolated glomeruli from NTS-challenged and normal mice with or with no EGFR antagonist provided evidence for FGFR-dependent modulation of STAT3 activation in vivo (FIG. 7A).

To examine whether IL-6 and HB-EGF could activate STAT3 pathway directly in podocytes, the inventors blocked IL-6 and EGFR in cultured primary podocytes and then performed western blotting to determine STAT3 phosphorylation (Tyr705), which is a marker of activation of STAT3 signaling. Cultured podocytes display features of dedifferentiation with acquired proliferative capacity and constitutive EGFR and STAT3 activation. The inventors found that both specific kinase inhibitor of EGFR, AG1478 and anti-mIL-6 monoclonal antibody blunted STAT3 phosphorylation (FIG. 7B). Furthermore, these data indicate that IL-6 receptor (IL-6R) and EGFR pathway are tonically activated by autocrine synthesis of ligands by activated podocytes. Taken together, these data suggest that both EGFR and IL-6R may stimulate STAT3 pathway in activated podocytes in vitro and in vivo during crescentic RPGN.

STAT3 Activity Upregulates miR-92a in Podocytes During RPGN.

Because of the potent action of STAT3 on podocyte phenotype, the inventors suspected that STAT3 activation may target a large set of genes through modulation of microRNAs. In particular, STAT3 has been shown to activate several microRNAs in various diseases (15, 28). Because of the presence of highly conserved STAT3-binding site in the promoter region of the miR-17/92 gene, the inventors have studied the expression of miR-17/92a in experimental crescentic GN. The inventors found a widespread upregulation of miR-92a throughout kidney from NTS-challenged nephritic Pod-Stat3 WT, particularly in glomerular cells. MicroRNA-92a expression was not increased in Stattic-treated Pod-Stat3 WT animals nor in Pod-Stat3 lox mice. The upregulation shown by miR-92a in situ hybridization on kidney sections was confirmed by RT-qPCR (FIG. 8A). Consistent with findings on mouse model, miR-92a was significantly upregulated in kidney from 4 patients diagnosed with crescentic glomerulonephritis caused by ANCA-associated vasculitides compared to controls subjects (FIG. 8B).

miR-92a Inhibition in Vitro Decreases Podocyte Proliferation

To decipher the role of miR-92a on podocyte function, the inventors inhibited miR-92a expression in primary culture of podocytes (change, −71%) (FIG. 9A). Anti-miR-92a did not affect STAT3 protein level, suggesting that STAT3 is an upstream regulator of miR-92a (data not shown). Delivery of anti-miR-92a to podocytes caused a decrease in outgrowth (FIG. 9B) and in Ki67 mRNA level (FIG. 9C), compared to control cells or transfected with an anti-miR control. Therefore, miR-92a seems to be involved in the regulation of podocyte proliferation. Thus, the inventors next searched for potential targets of miR-92a in target prediction algorithms as miRanda, miRWalk and TargetScan. The inventors focused on genes that have been previously related to podocyte proliferation. Among potential candidates, the inventors found a member of the Cip!Kip family, the p57/Kip2/Cyclin-dependent kinase inhibitor 1C, a tight-binding inhibitor of several G1 cyclin/Cdk complexes and a negative regulator of cell proliferation (29, 30).

Overexpressing p57 leads to GI phase cell cycle arrest and different studies have shown that p57 is constitutively expressed in mature podocytes (31, 32) as the inventors also found, and decrease in p57 protein expression during glomerular disease is associated with an increase in podocyte proliferation (33). The inventors studied the p57 protein expression by western blot and immunofluorescence in anti-miR-92a transfected podocytes (FIG. 9D). In this condition, our results show an increase in p57 expression, correlating with a decrease in podocyte proliferation.

Inhibition of miR-92a in Mice Ameliorates Glomerular Injury.

Chemically engineered oligonucleotides, termed 'antagomirs', arc efficient and specific silencers of endogenous miRNAs in mice. It was previously demonstrated that tiny, miRNA-inhibiting antagomirs (anti-miR) are taken up into the kidney cortex after intravenous injection into mice (34).

The inventors then tested the feasibility of this anti-miR-92a strategy to prevent the development of RPGN. The inventors induced RPGN in mice and injected anti-miR-92a. Anti-miR-92a injections allowed for specific inhibition of miR-92a expression in isolated glomeruli during RPGN (FIG. 10) without modify levels of others miR of 17-92 cluster. Compared with either control anti-miR (NTS+anti-miR-ctrl) or vehicle only (NTS), anti-miR92a administration led to less glomerular injury, shown by less glomerular crescents formation (-44%, P<0.05 vs NTS+anti-miR-ctrl) and a strong decrease in urinary albumin excretion (FIG. 11A) and kidney dysfunction (FIG. 11B).

To determine whether miR-92a inhibition could have an effect on p57 expression in vivo, the inventors performed immunostaining for p57 on kidney sections of mice injected with anti-miR-92a. Induction of glomerulonephritis induced a decrease in p57 expression in glomeruli that was rescued by anti-miR-92a administration (FIG. 11C).

The inventors validated these results in curative strategy by antagomir injection on days 4, 5 and 8 after NTS (FIGS. 12 A-E).

Discussion

RPGN with extracapillary proliferation of epithelial glomerular cells is a major clinical problem because it does not fully respond to immunosuppressive therapy and leads to chronic renal failure. As RPGN involves primarily the podocytes reaction to immune injury, deeper insights into the stabilization mechanisms of podocytes are important, and the question of a potential role of regulatory miRNAs arises. However, the role of specific miRNAs, to the best of our knowledge, has not been addressed. Comparing signaling cascade profiling in primary podocytes, in a mouse model of RPGN and random human kidney samples diagnosed with crescentic GN, the inventors identified pathways promoting miR-92a upregulation, in particular EGFR-mediated STAT3 activation in podocytes. The studies presented here systematically demonstrate the involvement of miR-92a in the deleterious response to immune injury that leads to glomerular destruction and functional demise. Our studies further identified a key miR-92a target as p57/Kip2/Cyclin-dependent kinase inhibitor 1C that is involved in cell cycle regulation and control of quiescent state of podocytes.

The miR-92a is part of the miR-17-92 cluster. The miR-17-92 cluster is a polycistrionic miRNA that encodes 6 miRNAs (35). Mice deficient for miR-17-92 die rapidly after birth with described cardiac and lung abnormalities. Thus, this study suggested a physiological importance role of this cluster in development. Interestingly, miR-17-92 was described as an oncogenic miRNA cluster, first as involved in B-cell lymphoma. However, other studies have reported contrasting rotes for these miRNAs, both as a cluster and as individually miRNAs. Among the members in the cluster, miR-92a is the least characterized subunit. The role of specific miRNAs and in particular miR-92a, to the best of our knowledge, has not been addressed in crescentic RPGN.

Here, for the first time the inventors provided data about miR-92a upregulation in this severe kidney disease. Given that miRNAs are conserved, with regard to both evolution and function, our observation of a common crescentic miRNA expression pattern in murine RPGN and human crescentic lesions is likely to have significant pathogenic, diagnostic, and/or therapeutic implications in human RPGNs.

A novel finding of our study is that we identify STAT3 as a key regulator in podocytes that activates miR-92a in glomeruli during crescentic RPGN. Phosphorylated forms of STAT3 (p-STAT3) are found at low level in normal glomeruli (36). Expression of the JAK/Stat3 pathway in non podocyte cells has been involved in several models of glomerular diseases. P-STAT3 involvement in inflammatory response of cultures mesangial cells in vitro has been demonstrated (37, 38) and followed by studies of experimental mesangial diseases. STAT3 activation was again found in mesangial cells and influenced the progression of diabetic nephropathy (39, 40) and of Thyl glomerulonephritis (41). Inhibition of JAK2 signaling ameliorated the course of adriamycin nephropathy in mouse (42). However, the dramatic changes in podocyte phenotype occurring in crescentic RPGN are absent in these models, and no conclusion regarding a potential role of STAT3 in RPGN could be drawn from these studies. Interestingly, evidence that STAT3 activation modulates podocyte phenotype has been recently brought in the specific setting of HIV-associated nephropathy (HIVAN). Although the mechanisms of RPGN differ from those of HIVAN in many points, these two diseases share some similarities in podocyte changes. Indeed, podocytes loose their specific markers and proliferate in both RPGN and HIVAN (4, 5, 43, 44). Specific mechanisms are at play promoting HIVAN, with evidence that the HIV-1 protein Nef activates the STAT3 and MAPK1,2 pathways, fostering podocyte proliferation and dedifferentiation (45). In HTV-1 transgenic mice (Tg26), renal injury was alleviated by suppression of STAT3 limited to podocytes (46). Very recently, these authors published similar findings than ours, using a mouse model of podocyte-specific deletion of Stat3 in an accelerated model of NTS-induced RPGN (47). Altogether, these findings indicate that STAT3 orchestration of podocyte phenotype may be a general paradigm for proliferative extracapillary diseases and our study provides additional insights and relevance to human disease with proof of principle for potential therapy since systemic STAT3 blockade with Stattic mimicked the protective action of podocyte targeted Stat3 gene deletion and prevented renal failure. Observation that STAT3 blockade by Stattic inhibited proliferation and migration of cultured primary podocytes indicate that STAT3 stimulates alteration of podocyte phenotype such as seen in RPGN. The potent anti-proliferative action provided by STAT3 deficiency was further demonstrated in vivo since Stczt3 specific deletion in podocytes resulted in reduced expression of the proliferation markers PCNA and Ki67 in renal cortex and in podocytes and consistently prevented crescent formation during RPGN.

Another salient result in our study was the observation that STAT3 activation was induced not only in mouse but also in human RPGN associated with ANCA-associated vasculitis. The inventors found expression of phosphorylated STAT3 in crescentic glomeruli of patients with RPGN whereas no or faint staining for phosphorylated STAT3 was detected in normal glomeruli. Although phosphorylated STAT3 was mainly detected in podocytes and glomerular crescents, positive immunostaining was also observed in some parietal epithelial cells. Therefore, STAT3 may be also involved in the proliferation of parietal epithelial cells, which is known to contribute to crescent formation (3).

The inventors did not investigate whether STAT3 activation was involved in the loss of podocyte differentiation markers like podocin, nephrin and synaptopodin that typically occurs along with de novo expression of proliferation markers in RPGN (5, 6). In experimental HIVAN, Tg26 mice with reduced STAT3 activity showed preservation of synaptopodin, podocin, and WT-1 expression. Podocyte-specific deletion of STAT3 resulted in similar prevention of podocyte dedifferentiation in Tg26 mice (46). A limitation of our study may be that the inventors did not examine the effect of STAT3 activation on vascular endothelial growth factor (VEGF) expression in our model. STAT3 was shown to mediate HIV-induced VEGF expression in podocytes, which may represent a critical step in the development of HIVAN (48, 49). However, a role for increased VEGF expression in glomerular injury seems less likely in RPGN than in HIVAN. Indeed, podocyte-specific overexpression of VEGF in mouse led to collapsing glomerulopathy, recapitulating the phenotype of HIVAN, but not RPGN (50). In addition, blockade of VEGF did not improve but rather worsened the course of RPGN in rat (51). At last, our transcriptome analysis of isolated glomeruli show diminished VEGFA and receptors mRNA expression in nephritic mice when compared to unchallenged mice (data not shown). Thus, altogether, these data suggest that STAT3 activation is part of distinct signaling networks in podocytes in RPGN and in HIVAN.

The inventors further found pathways upstream of STAT3 activation in podocytes. The inventors recently demonstrated in a mouse model of anti-glomerular basement membrane (anti-GBM) glomerulonephritis that the lack of EGFR ligand HB-EGF or pharmacological blockade of EGFR or genetic deletion of Egfr alleles in podocytes prevented crescent formation and markedly alleviated the course of RPGN (8). The evidence demonstrating functional or direct association between EGFR and STAT3 is based primarily on work done in cell lines expressing high levels of EGFR, such as A431, and head and neck squamous cell carcinoma (HNSCC) cells (11, 19, 27, 52). Given that EGFR-mediated intracellular events can be transduced through activation of STAT3 (10, 11, 19, 20, 53), the inventors investigated whether inhibition of EGFR could influence STAT3 activation in RPGN. Selective EGFR kinase inhibitor erlotinib efficiently blocked EGFR phosphorylation in the kidney cortex and also blunted STAT3 phosphorylation in podocytes. In the case of RPGN, EGFR autocrine/paracrine activation is promoted by derepression of the Hbegf gene in podocytes and parietal epithelial cells (8, 54). Interestingly, autocrine activation of STAT3 by HB-EGF has been reported in breast cancer lines (27). However, despite apparent complete inhibition of EGFR, the phosphorylated form of STAT3 remained low but detectable, indicating that STAT3 activation was not entirely mediated through EGFR signaling. In line with these results in vivo, the inventors observed in primary cultures of podocytes that STAT3 phosphorylation was enhanced by HB-EGF, and was decreased by the EGFR kinase inhibitor AG1478. Furthermore, neutralization of IL-6 also blunted STAT3 phosphorylation. This suggests that cultured primary podocyte acquiring an 'activated' phenotype display autocrine activation of both EGFR and IL-6R pathways leading to downstream STAT3 activation with proliferation.

Therefore, it appears that EGFR and IL-6 signaling are significant mechanisms driving STAT3 activation in RPGN and in cultured podocytes with upregulation of miR-92a expression. In line with this finding, a case of anti-neutrophil cytoplasmic antibody (ANCA)—associated crescentic RPGN has been successfully treated using anti-IL-6 receptor antibody (55).

The inventors also identified a relevant miR-92a target for podocyte proliferation. In contrast to immature podocytes, which proliferate during glomerular development in utero, differentiated podocytes have a terminally differentiated quiescent phenotype (56). The maintenance of a differentiated phenotype is required for podocytes to perform their specialized functions (56). Using three independent target prediction algorithms, the inventors identified p57 as a miR-92a target. The CDK inhibitor p57 regulates cell proliferation and differentiation (57). P57 is typically expressed in differentiated and postmitotic nonrenal cells, and Shankland et al. and others have shown that there is de novo expression of p57 in podocytes during glomerulogenesis that coincides with p27 expression and with podocyte acquisition of a terminally differentiated phenotype (33, 58). Loss of p57 expression in podocytes was early recognized a feature of proliferative glomerular diseases (5, 59-61) although the mechanism remained elusive. The inventors cannot exclude that other miR-92a targets such as PTEN (62) or Reck (16) could be involved in podocyte dedifferentiation process. Nevertheless, the inventors confirmed that a decrease or absence of p57 immunostaining was associated with damage and proliferative podocyte phenotype in experimental RPGN. Importantly, a decrease in the level of p57 and a corresponding de novo expression of Ki67 coincided with podocyte proliferation in vitro and in vivo as observed with administration of antagomir that specifically silence miR-92a and effectively reversed the deleterious effects of miR-92a in kidney injuries.

Our combined results obtained from in vitro experiments, mouse models and human tissues indicate that increased expression of miR-92a can initiate a cascade of podocyte-destabilizing molecular events starting with the downregulation of p57 and proliferation. Moreover, specific blockade of miR-92a in vivo by an antagomir markedly reduced proteinuria, crescent formation and renal failure. Although this treatment showed a preventive effect in our mouse model, it remains to be seen whether this holds true for human RPGN as well.

In summary, the inventors provide evidence for a new pathogenic mechanism for RPGN that is driven by STAT3-mediated upregulation of miR-92a and decrease in p57, unlocking podocyte ability to proliferate with ensuing proteinuria, destruction of the glomerular filtration barrier and declining renal function.

Example 2

High expression of miR-92a in human kidneys with RPGN

To evaluate the clinical relevance of the results obtained in the mouse model, the inventors analyzed miR-92a expression by in situ hybridization and RT-PCR in paraffin-embedded tissue of renal biopsies from patients with RPGN and control patients with non proliferative glomerulopathies (Table 1). MiR-92a labeling was weak and restricted to the endothelium in control human kidneys (non-crescentic glomerular disease). However, miR-92a was significantly upregulated in kidney biopsies from patients with RPGN, regardless of its etiology. In situ hybridization revealed the expression of miR-92a in glomerular cells of patients with RPGN, particularly in podocytes and crescents and to a lesser extent in parietal epithelial cells. RT-qPCR analysis revealed that the expression of miR-92a was three to five fold higher in samples from patients with RPGN of various etiologies including stage III and IV lupus nephritis (Lup), microscopic polyangiitis (MPA) and granulomatosis with polyangiitis (GPA) than those from patients diagnosed with noncrescentic glomerulopathies, other chronic proteinuric glomerular diseases including minimal change disease (MCD) and membranous nephropathy (MM). The inventors observed a similar pattern of miR-92a expression in all kidney samples from patients with RPGN regardless of immunological etiology. These results show that miR-92a is highly abundant, sometimes in a sustained fashion, in conditions associated with glomerular epithelial cell proliferation and crescent formation.

TABLE 1

Patients' clinical details

| Gender | Age | Diagnosis | Relapse | Treatment |
|---|---|---|---|---|
| F | 29 | Minimal Change Disease | Relapse | Corticosteroids |
| F | 30 | Minimal Change Disease | Relapse | No treatment |
| M | 66 | Minimal Change Disease | First episode | No treatment |
| F | 31 | Minimal Change Disease | First episode | No treatment |
| F | 30 | Membranous Nephropathy | First episode | No treatment |
| M | 46 | Membranous Nephropathy | First episode | No treatment |
| M | 50 | Membranous Nephropathy | First episode | No treatment |
| M | 62 | Micro-polyangiitis MPO-ANCA-positive | First episode | No treatment |
| M | 78 | Micro-polyangiitis PR3-ANCA-positive | First episode | Corticosteroids |
| M | 52 | Micro-polyangiitis MPO-ANCA-positive | First episode | No treatment |
| F | 46 | Micro-polyangiitis MPO-ANCA-positive | First episode | No treatment |
| M | 47 | Micro-polyangiitis MPO-ANCA-positive | First episode | No treatment |
| F | 58 | Micro-polyangiitis MPO-ANCA-positive | First episode | No treatment |
| M | 44 | Micro-polyangiitis ANCA-positive | First episode | No treatment |
| M | 68 | Granulomatosis with polyangiitis | First episode | Corticosteroids |
| M | 71 | Granulomatosis with polyangiitis | First episode | No treatment |
| M | 55 | Granulomatosis with polyangiitis | Relapse | Corticosteroids |
| F | 35 | Lupus nephritis (class IV) | Relapse | Corticosteroids |
| F | 27 | Lupus nephritis (class IV) | Relapse | Corticosteroids |
| M | 17 | Lupus nephritis (class IV) | First episode | No treatment |
| F | 41 | Lupus nephritis (class III) | Relapse | Corticosteroids |
| F | 25 | Lupus nephritis (class III) | First episode | No treatment |

REFERENCES

Throughout this application, various references describe the state of the art to which this invention pertains. The disclosures of these references are hereby incorporated by reference into the present disclosure.

1. Couser, W. G. 1988. Rapidly progressive glomerulonephritis: classification, pathogenetic mechanisms, and therapy. Am J Kidney Dis 11:449-464.
2. Jennette, J. C., and Thomas, D. B. 2001. Crescentic glomerulonephritis. Nephrol Dial Transplant 16 Suppl 6:80-82.
3. Smeets, B., Uhlig, S., Fuss, A., Mooren, F., Wetzels, J. F., Floege, J., and Moeller, M. J. 2009. Tracing the origin of glomerular extracapillary lesions from parietal epithelial cells. J Am Soc Nephrol 20:2604-2615.
4. Thorner, P. S., Ho, M., Eremina, V., Sado, Y., and Quaggin, S. 2008. Podocytes contribute to the formation of glomerular crescents. J Am Soc Nephrol 19:495-502.
5. Bariety, J., Bruneval, P., Meyrier, A., Mandet, C., Hill, G., and Jacquot, C. 2005. Podocyte involvement in human immune crescentic glomerulonephritis. Kidney Int 68:1109-1119.
6. Moeller, M.J., Soofi, A., Hartmann, I., Le Hir, M., Wiggins, R., Kriz, W., and Holzman, L. B. 2004. Podocytes populate cellular crescents in a murine model of inflammatory glomerulonephritis. J Am Soc Nephrol 15:61-67.
7. Ding, M., Cui, S., Li, C., Jothy, S., Haase, V., Steer, B. M., Marsden, P. A., Pippin, J., Shankland, S., Rastaldi, M. P., et al. 2006. Loss of the tumor suppressor Vhlh leads to upregulation of Cxcr4 and rapidly progressive glomerulonephritis in mice. Nat Med 12:1081-1087.
8. Bollee, G., Flamant, M., Schordan, S., Fligny, C., Rumpel, E., Milon, M., Schordan, E., Sabaa, N., Vandermeersch, S., Galaup, A., et al. 2011. Epidermal growth factor receptor promotes glomerular injury and renal failure in rapidly progressive crescentic glomerulonephritis. Nat Med 17:1242-1250.
9. Mirmohammadsadegh, A., Hassan, M., Bardenheuer, W., Marini, A., Gustrau, A., Nambiar, S., Tannapfel, A., Bojar, H., Ruzicka, T., and Hengge, U.R. 2006. STAT5 phosphorylation in malignant melanoma is important for survival and is mediated through SRC and JAK1 kinases. J Invest Dermatol 126:2272-2280.
10. Park, O. K., Schaefer, T. S., and Nathans, D. 1996. In vitro activation of Stat3 by epidermal growth factor receptor kinase. Proc Natl Acad Sci U S A 93:13704-13708.
11. Shao, H., Cheng, H. Y., Cook, R. G., and Tweardy, D. J. 2003. Identification and characterization of signal transducer and activator of transcription 3 recruitment sites within the epidermal growth factor receptor. Cancer Res 63:3923-3930.
12. Aaronson, D. S., and Horvath, C. M. 2002. A road map for those who don't know JAK-STAT. Science 296:1653-1655.
13. Gebeshuber, C. A., Kornauth, C., Dong, L., Sierig, R., Seibler, J., Reiss, M., Tauber, S., Bilban, M., Wang, S., Kain, R., et al. 2013. Focal segmental glomerulosclerosis is induced by microRNA-193a and its downregulation of WT1. Nat Med 19:481-487.
14. Iliopoulos, D., Jaeger, S. A., Hirsch, H. A. Bulyk, M. L., and Struhl, K. 2010. STAT3 activation of miR-21 and miR-18 lb-1 via PTEN and CYLD are part of the epigenetic switch finking inflammation to cancer. Mol Cell 39:493-506.
15. Loffler, D., Brocke-Heidrich, K., Pfeifer, G., Stocsits, C., Hackermuller, J., Kretzschmar, A. K., Burger, R., Gramatzki, M., Blumert, C., Bauer, K., et al. 2007. Interleukin-6 dependent survival of multiple myeloma cells involves the Stat3-mediated induction of microRNA-21 through a highly conserved enhancer. Blood 110:1330-1333.
16. Lin, H. Y., Chiang, C. H., and Hung. W. C. 2013. STAT3 upregulates miR-92a to inhibit RECK expression and to promote invasiveness of lung cancer cells. Br J Cancer.
17. Brock, M., Trenkmann, M., Gay, R. E., Michel, B. A., Gay, S., Fischler, M., Ulrich, S., Speich, R., and Huber, L. C. 2009. Interleukin-6 modulates the expression of the bone morphogenic protein receptor type II through a novel STAT3-microRNA cluster 17/92 pathway. Circ Res 104: 1184-1191.

18. Zhong, Z., Wen, Z., and Daniell, J. E., Jr. 1994. Stat3: a STAT family member activated by tyrosine phosphorylation in response to epidermal growth factor and interleukin-6. Science 264:95-98.

19. Grandis, J. R., Drenning, S. D., Chakraborty, A., Zhou, M. Y., Zeng, Q., Pitt, A. S., and Tweardy, D.J. 1998. Requirement of Stat3 but not Stat1 activation for epidermal growth factor receptor-mediated cell growth In vitro. J Clin Invest 102:1385-1392.

20. Gao, S. P., Mark, K. G., Leslie, K., Pao, W., Motoi, N., Gerald, W. L., Travis, W. D., Bommann, W., Veach, D., Clarkson, B., et al. 2007. Mutations in the EGFR kinase domain mediate STAT3 activation via IL-6 production in human lung adenocarcinomas. J Clin Invest 117:3846-3856.

21. Lutticken, C., Wegenka, U. M., Yuan, J., Buschmann, J., Schindler, C., Ziemiecki, A., Harpur, A. G., Wilks, A. F., Yasukawa, K., Taga, T., et al. 1994. Association of transcription factor APRF and protein kinase Jak1 with the interleukin-6 signal transducer gp130. Science 263:89-92.

22. Kishimoto, T. 1994. Signal transduction through homo- or heterodimers of gp130. Stem Cells 12 Suppl 1:37-44; discussion 44-35.

23. Wegenka, U. M., Buschmann, J., Luttickcn, C., Heinrich, P. C., and Horn, F. 1993. Acute-phase response factor, a nuclear factor binding to acute-phase response elements, is rapidly activated by interleukin-6 at the posttranslational level. Mol Cell Biol 13:276-288.

24. Wehinger, J., Gouilleux, F., Groner, B., Finke, J., Mertelsmann, R., and Weber-Nordt, R. M. 1996. IL-10 induces DNA binding activity of three STAT proteins (Stat1, Stat3, and StatS) and their distinct combinatorial assembly in the promoters of selected genes. FEBS Lett 394:365-370.

25. Weber-Nordt, R. M., Riley, J. K., Greenlund, A. C., Moore, K. W., Daniell, J. E., and Schreiber, R. D. 1996. Stat3 recruitment by two distinct ligand-induced, tyrosine-phosphorylated docking sites in the interleukin-10 receptor intracellular domain. J Biol Chem 271:27954-27961.

26. Finbloom, D. S., and Winestock, K. D. 1995. IL-10 induces the tyrosine phosphorylation of tyk2 and Jak1 and the differential assembly of STAT1 alpha and STAT3 complexes in human T cells and monocytes. J Immunol 155: 1079-1090.

27. Sartor, C. I., Dziubinski, M. L., Yu, C. L., Jove, R., and Ethier, S. P. 1997. Role of epidermal growth factor receptor and STAT-3 activation in autonomous proliferation of SUM-102PT human breast cancer cells. Cancer Res 57:978-987.

28. Bourguignon, L. Y., Earle, C., Wong, G., Spcvak, C. C., and Krueger, K. 2012. Stem cell marker (Nanog) and Stat-3 signaling promote MicroRNA-21 expression and chemoresistance in hyaluronan/CD44-activated head and neck squamous cell carcinoma cells. Oncogene 31:149-160.

29. Matsuoka, S., Edwards, M. C., Bai, C., Parker, S., Zhang, P., Baldini, A., Harper, J. W., and Elledge, S. J. 1995. p57KIP2, a structurally distinct member of the p21CIP1 Cdk inhibitor family, is a candidate tumor suppressor gene. Genes Dev 9:650-662.

30. Lee, M. H., Reynisdottir, I., and Massague, J. 1995. Cloning of p57KIP2, a cyclin-dependent kinase inhibitor with unique domain structure and tissue distribution. Genes Dev 9:639-649.

31. Shankland, S. J., and Wolf, G. 2000. Cell cycle regulatory proteins in renal disease: role in hypertrophy, proliferation, and apoptosis. Am J Physiol Renal Physiol 278:F515-529.

32. Nagata, M., Nakayama, K., Terada, Y., Hoshi, S., and Watanabe, T. 1998. Cell cycle regulation and differentiation in the human podocyte lineage. Am J Pathol 153:1511-1520.

33. Hirornura, K., Haseley, L. A., Zhang, P., Monkawa, T., Durvasula, R., Petermann, A. T., Alpers, C. E., Mundel, P., and Shankland, S. J. 2001. Podocyte expression of the CDK-inhibitor p57 during development and disease. Kidney Int 60:2235-2246.

34. Krutzfeldt, J., Rajewsky, N., Braich, R., Rajeev, K. G., Tuschl, T., Manoharan, M., and Stoffel, M. 2005. Silencing of microRNAs in vivo with 'antagomirs'. Nature 438:685-689.

35. Mendell, J. T. 2008. miRiad roles for the miR-17-92 cluster in development and disease. Cell 133:217-222.

36. Arakawa, T., Masaki, T., Hirai, T., Doi, S., Kuratsune, M., Arihiro, K., Kohno, N., and Yorioka, N. 2008. Activation of signal transducer and activator of transcription 3 correlates with cell proliferation and renal injury in human glomerulonephritis. Nephrol Dial Transplant 23:3418-3426.

37. Yu, Z., and Kone, B. C. 2004. The STAT3 DNA-binding domain mediates interaction with NF-kappaB p65 and inducible nitric oxide synthase transrepression in mesangial cells. J Am Soc Nephrol 15:585-591.

38. Zhang, W., Chen, X., Shi, S., Wei, R., Wang, J., Yamanaka, N., and Hong, Q. 2005. Expression and activation of STAT3 in chronic proliferative immune complex glomerulonephritis and the effect of fosinopril. Nephrol Dial Transplant 20:892-901.

39. Marrero, M. B., Banes-Bcrccli, A. K., Stern, D. M., and Eaton, D. C. 2006. Role of the JAK/STAT signaling pathway in diabetic nephropathy. Am J Physiol Renal Physiol 290:F762-768.

40. Wang, X., Shaw, S., Amiri, F., Eaton, D. C., and Marrero, M. B. 2002. Inhibition of the Jak/STAT signaling pathway prevents the high glucose-induced increase in tgf-beta and fibronectin synthesis in mesangial cells. Diabetes 51:3505-3509.

41. Yanagita, M, Arai, H., Nakano, T., Ohashi, K., Mizuno, K., Fukatsu, A., Doi, T., and Kita, T. 2001. Gas6 induces mesangial cell proliferation via latent transcription factor STAT3. J Biol Chem 276:42364-42369.

42. Li, R., Yang, N., Zhang, L., Huang, Y., Zhang, R., Wang, F., Luo, M., Liang, Y., and Yu, X. 2007. Inhibition of Jak/STAT signaling ameliorates mice experimental nephrotic syndrome. Am J Nephrol 27:580-589.

43. Barisoni, L., Kriz, W., Mundel, P., and D'Agati, V. 1999. The dysregulated podocyte phenotype: a novel concept in the pathogenesis of collapsing idiopathic focal segmental glomerulosclerosis and HIV-associated nephropathy. J Am Soc Nephrol 10:51-61.

44. Barisoni, L., Mokrzycki, M., Sablay, L., Nagata, M., Yamase, H., and Mundcl, P. 2000. Podocyte cell cycle regulation and proliferation in collapsing glomerulopathies. Kidney Int 58:137-143.

45. He, J.C., Husain, M., Sunamoto, M., D'Agati, V. D., Klotman, M. E., lyengar, R., and Klotman, P. E. 2004. Nef stimulates proliferation of glomerular podocytes through activation of Src-dependent Stat3 and MAPK1,2 pathways. J Clin Invest 114:643-651.

46. Gu, L., Dai, Y., Xu, J., Mallipattu, S., Kaufman, L., Klotman, P. E., He, J. C., and Chuang, P. Y. 2013. Deletion of podocyte STAT3 mitigates the entire spectrum of HIV-1-associated nephropathy. AIDS.

47. Dai, Y., Gu, L., Yuan, W., Yu, Q., Ni, Z., Ross, M. J., Kaufman, L., Xiong, H., Salant, D. J., He, J. C., et al. 2013. Podocyte-specific deletion of signal transducer and activator of transcription 3 attenuates nephrotoxic serum-induced glomerulonephritis. Kidney Int.

48. Feng, X., Lu, T. C., Chuang, P. Y., Fang, W., Ratnam, K., Xiong, H., Ouyang, X., Shen, Y., Levy, D. E., Hyink, D., et al. 2009. Reduction of Stat3 activity attenuates HIV-induced kidney injury. J Am Soc Nephrol 20:2138-2146.

49. Korgaonkar, S. N., Feng, X., Ross, M. D., Lu, T. C., D'Agati, V., Iyengar, R., Klotman, P. E., and He, J. C. 2008. HIV-1 upregulates VEGF in podocytes. J Am Soc Nephrol 19:877-883.

50. Eremina, V., Sood, M., Haigh, J., Nagy, A., Lajoic, G., Ferrara, N., Gerber, H. P., Kikkawa, Y., Miner, J. H., and Quaggin, S. E. 2003. Glomerular-specific alterations of VEGF-A expression lead to distinct congenital and acquired renal diseases. J Clin Invest 111:707-716.

51. Hara, A., Wada, T., Furuichi, K., Sakai, N., Kawachi, H., Shimizu, F., Shibuya, M., Matsushima, K., Yokoyama, H., Egashira, K., et al. 2006. Blockade of VEGF accelerates proteinuria, via decrease in nephrin expression in rat crescentic glomerulonephritis. Kidney Int 69:1986-1995.

52. Zhang, T., Ma, J., and Cao, X. 2003. Grb2 regulates Stat3 activation negatively in epidermal growth factor signalling. Biochem J 376:457-464.

53. Sordella, R., Bell, D. W., Haber, D. A., and Settleman, J. 2004. Gefitinib-sensitizing EGFR mutations in lung cancer activate anti-apoptotic pathways. Science 305:1163-1167.

54. Flamant, M., Bollee, G., Henique, C., and Tharaux, P.L. 2012. Epidermal growth factor: a new therapeutic target in glomerular disease. Nephrol Dial Transplant 27:1297-1304.

55. Sumida, K., Ubara, Y., Suwabe, T., Hayami, N., Hiramatsu, R., Hasegawa, E., Yamanouchi, M., Hoshino, J., Sawa, N., Takemoto, F., et al. 2011. Complete remission of myeloperoxidase-anti-neutrophil cytoplasmic antibody-associated crescentic glomerulonephritis complicated with rheumatoid arthritis using a humanized anti-interleukin 6 receptor antibody. Rheumatology (Oxford) 50:1928-1930.

56. Pavenstadt, H., Kriz, W., and Kretzler, M. 2003. Cell biology of the glomerular podocyte. Physiol Rev 83:253-307.

57. Zhang, P., Wong, C., DePinho, R. A., Harper, J. W., and Elledge, S. J. 1998. Cooperation between the Cdk inhibitors p27(KIP1) and p57(KIP2) in the control of tissue growth and development. Genes Dev 12:3162-3167.

58. Shankland, S. J., Eitner, F., Hudkins, K. L., Goodpaster, T., D'Agati, V., and Alpers, C. E. 2000. Differential expression of cyclin-dependent kinase inhibitors in human glomerular disease: role in podocyte proliferation and maturation. Kidney Int 58:674-683.

59. Srivastava, T., Garola, R. E., and Singh, H. K. 2006. Cell-cycle regulatory proteins in the podocyte in collapsing glomerulopathy in children. Kidney Int 70:529-535.

60. Wang, S., Kim, J. H., Moon, K. C., Hong, H. K., and Lee, H. S. 2004. Cell-cycle mechanisms involved in podocyte proliferation in cellular lesion of focal segmental glomerulosclerosis. Am J Kidney Dis 43:19-27.

61. Baricty, J., Hill, G. S., Mandct, C., Irinopoulou, T., Jacquot, C., Mcyricr, A., and Bruneval, P. 2003. Glomerular epithelial-mesenchymal transdifferentiation in pauci-immune crescentic glomerulonephritis. Nephrol Dial Transplant 18:1777-1784.

62. Zhang, G., Zhou, H., Xiao, H., Liu, Z., Tian, H., and Zhou, T. 2013. MicroRNA-92a Functions as an Oncogene in Colorectal Cancer by Targeting PTEN. Dig Dis Sci.

63. Moeller, M. J., Sanden, S. K., Soofi, A., Wiggins, R. C., and Holzman, L. B. 2003. Podocyte-specific expression of cre recombinase in transgenic mice. Genesis 35:39-42.

64. Moh, A., Iwamoto, Y., Chai, G. X., Zhang, S. S., Kano, A., Yang, D. D., Zhang, W., Wang, J., Jacoby, J. J., Gao, B., et al. 2007. Role of STAT3 in liver regeneration: survival, DNA synthesis, inflammatory reaction and liver mass recovery. Lab Invest 87:1018-1028.

65. Schust, J., Sperl, B., Hollis, A., Mayer, T. U., and Berg, T. 2006. Stattic: a small-molecule inhibitor of STAT3 activation and dimerization. Chem Biol 13:1235-1242.

66. Bonauer, A., Carmona, G., Iwasaki, M., Mione, M., Koyanagi, M., Fischer, A., Burchfield, J., Fox, H., Doebele, C., Ohtani, K., et al. 2009. MicroRNA-92a controls angiogenesis and functional recovery of ischemic tissues in mice. Science 324:1710-1713.

67. Sengul, A., Santisuk, R., Xing, W., and Kesavan, C. 2013. Systemic administration of an antagomir designed to inhibit miR-92, a regulator of angiogenesis, failed to modulate skeletal anabolic response to mechanical loading. Physiol Res 62:221-226.

68. Jenette J C and Thomas D B. Crescentic glomerulonephritis. Nephrol Dial Transplant. 2001;16 Suppl 6:80-2.

69. Moeller M J, Soofi A, Hai tmann I, et al. Podocytes populate cellular crescents in a murine model of inflammatory glomerulonephritis. J Am Soc Nephrol 2004; 15:61-67.

70. Tarzi R M, Cook H T, Pusey C D. Crescentic glomerulonephritis: new aspects of pathogenesis. Semin Nephrol. 2011 July; 31(4):361-8.

71. King S K, Jeansson M, Quaggin S E et al. New insights into the pathogenesis of cellular crescents. Current Opinion in Nephrology and Hypertension 2011, 20:258-262.

72. Robert M. Kliegman, M D, Bonita M. D. Stanton, M D, Joseph St. Geme, Nina Schor and Richard E. Behrman, M D. Chapter 510 -Rapidly Progressive (Crescentic) Glomerulonephritis. Nelson Textbook of Pediatrics, 19th Edition—Saunders Title, ISBN: 978-1-4377-0755-7.

73. Bariety J, Nochy D, Mandet C, Jacquot C, Glotz D, Meyrier A: Podocytes undergo phenotypic changes and express macrophagic-associated markers in idiopathic collapsing glomerulopathy. Kidney Int 53 : 918-925, 1998.

74. Srivastava T, Garola R E, Singh H K: Cell-cycle regulatory proteins in the podocyte in collapsing glomerulopathy in children. Kidney Int 70 : 529-535, 2006.

75. Dijkman H B, Weening J J, Smeets B, Verrijp K C, van Kuppevelt T H, Assmann K K, Steenbergen E J, Wetzels J: Proliferating cells in HIV and pamidronate-associated collapsing focal segmental glomerulosclerosis are parietal epithelial cells. Kidney Int 70 : 338-344, 2006.

76. Albaqumi M, Barisoni L. Current views on collapsing glomerulopathy. J Am Soc Nephrol. 2008 July; 19(7): 1276-81.

The invention claimed is:

1. A method of preventing or treating extracapillary glomerulonephritis in a subject in need thereof comprising the steps of: i) providing a sample from a subject, ii) measuring the expression level of miR-92a in the sample obtained at step i), iii) comparing said expression level measured in step ii) with a control, wherein high expression level of miR-92a is indicative of subject having or at risk of having or developing an extracapillary glomerulonephritis, and iv) treating said subject having or at risk of having or developing an extracapillary glomerulonephritis with a miR-92a inhibitor compound and, optionally, an extracapillary glomerulonephritis treatment, wherein said miR-92a inhibitor compound is a nucleic acid that hybridizes with miR-92a.

2. The method according to claim 1 wherein said extracapillary glomerulonephritis is a rapidly progressive glomerulonephritis and said extracapillary glomerulonephritis treatment is a rapidly progressive glomerulonephritis treatment.

3. The method according to claim 2 wherein said rapidly progressive glomerulonephritis (RPGN) treatment is cyclophosphamide, plasmapheresis, anti-CD20 antibody, mycophenolate mofetil and corticosteroids such as methylprednisolone or prednisone.

4. The method according to claim 1 wherein said extracapillary glomerulonephritis is a collapsing glomerulopathy and said extracapillary glomerulonephritis treatment is a collapsing glomerulopathy treatment.

5. The method according to claim 4 wherein said collapsing glomerulopathy (CG) treatment is steroids or cyclosporine, angiotensin converting enzyme inhibitors and/or angiotensin II receptor blockers, anti-HIV therapy, lipid lowering agents and mycophenolate mofetil.

6. The method of claim 1, wherein the miR-92a inhibitor compound is selected from the group consisting of double-stranded RNA, antagomirs, antisense nucleic acids and enzymatic RNA molecules.

7. The method of claim 1, wherein the miR-92a inhibitor compound is encoded by a vector that is administered to the subject.

* * * * *

SEQUENCE LISTING

<160> NUMBER OF SEQ ID NOS: 8

<210> SEQ ID NO 1

```
<211> LENGTH: 78
<212> TYPE: RNA
<213> ORGANISM: Homo sapiens

<400> SEQUENCE: 1 cuucuacac agguugggau cgguugcaau gcuguguuuc uguaugguau ugcacuuguc    60
ccggccuguu gaguuugg                                                 78

<210> SEQ ID NO 2
<211> LENGTH: 23
<212> TYPE: RNA
<213> ORGANISM: Homo sapiens

<400> SEQUENCE: 2
agguugggau cgguugcaau gcu                                           23

<210> SEQ ID NO 3
<211> LENGTH: 22
<212> TYPE: RNA
<213> ORGANISM: Homo sapiens

<400> SEQUENCE: 3
uauugcacuu gucccggccu gu                                            22

<210> SEQ ID NO 4
<211> LENGTH: 75
<212> TYPE: RNA
<213> ORGANISM: Homo sapiens

<400> SEQUENCE: 4
ucaucccugg gugggauuu guugcauuac uuguguucua auaaaguau ugcacuuguc     60 ccggccugug aaga                                                     75

<210> SEQ ID NO 5
<211> LENGTH: 22
<212> TYPE: RNA
<213> ORGANISM: Homo sapiens

<400> SEQUENCE: 5 ggugggau uuguugcauu ac                                              22

<210> SEQ ID NO 6
<211> LENGTH: 22
<212> TYPE: RNA
<213> ORGANISM: Homo sapiens

<400> SEQUENCE: 6
uauugcacuu gucccggccu gu                                            22

<210> SEQ ID NO 7
<211> LENGTH: 22
<212> TYPE: RNA
<213> ORGANISM: Artificial
<220> FEATURE:
<223> OTHER INFORMATION: Synthetic anti-miR-ctrl

<400> SEQUENCE: 7
aaggcaagcu gacccugaag uu                                            22

<210> SEQ ID NO 8
<211> LENGTH: 21
<212> TYPE: RNA
<213> ORGANISM: Artificial
```

```
<220> FEATURE:
<223> OTHER INFORMATION: Synthetic anti-miR-92a

<400> SEQUENCE: 8
caggccggga caagugcaau a                                              21
```